(12) United States Patent
Sperling

(10) Patent No.: US 9,897,541 B1
(45) Date of Patent: Feb. 20, 2018

(54) ATTENUATED TOTAL REFLECTION FLOW CELL

(71) Applicant: THE UNITED STATES OF AMERICA, AS REPRESENTED BY THE SECRETARY OF COMMERCE, Washington, DC (US)

(72) Inventor: Brent A. Sperling, New Market, MD (US)

(73) Assignee: THE UNITED STATES OF AMERICA, AS REPRESENTED BY THE SECRETARY OF COMMERCE, Washington, DC (US)

(*) Notice: Subject to any disclaimer, the term of this patent is extended or adjusted under 35 U.S.C. 154(b) by 0 days.

(21) Appl. No.: 15/411,322

(22) Filed: Jan. 20, 2017

(51) Int. Cl.
| | |
|---|---|
| *G01N 21/55* | (2014.01) |
| *G01N 21/552* | (2014.01) |
| *G01N 21/3577* | (2014.01) |
| *G01N 21/27* | (2006.01) |
| *G01N 21/35* | (2014.01) |

(52) U.S. Cl.
CPC ......... *G01N 21/552* (2013.01); *G01N 21/272* (2013.01); *G01N 21/3577* (2013.01); *G01N 2021/3595* (2013.01)

(58) Field of Classification Search
CPC ....... G01N 33/54373; G01N 33/54313; G01N 15/1434; G01N 2333/726; G01N 15/1404; G01N 21/553; G01N 21/31; G01N 21/636; G01N 2458/00; G01N 2500/02; G01N 2500/04; G01N 33/5308; G01N 33/56966
See application file for complete search history.

(56) References Cited

U.S. PATENT DOCUMENTS

| | | | | |
|---|---|---|---|---|
| 3,431,424 A | * | 3/1969 | Allen | G01N 21/05 250/576 |
| 2006/0274314 A1 | * | 12/2006 | Thomsen | B82Y 20/00 356/445 |
| 2011/0294139 A1 | * | 12/2011 | Takeda | G01N 15/1484 435/7.1 |
| 2012/0014837 A1 | * | 1/2012 | Fehr | B01L 3/502707 422/82.11 |
| 2014/0373606 A1 | * | 12/2014 | Kraiczek | G01N 33/54373 73/61.55 |

FOREIGN PATENT DOCUMENTS

WO  200202037086 A1  10/2001

OTHER PUBLICATIONS

N. Rochat et al., Multiple internal reflection infrared spectroscopy using two-prism coupling geometry: A convenient way for quantitative study of organic contamination on silicon wafers, Applied Physics Letters, Oct. 2, 2000, 2249-2251, vol. 77.
E. Karabudak et al., Disposable attenuated Total Reflection-Infrared Crystals from Silicon Wafer: A Versatile Approach to Surface Infrared Spectroscopy, Analytical Chemistry, 2013, 33-38, vol. 85.

\* cited by examiner

*Primary Examiner* — Michael P Stafira
(74) *Attorney, Agent, or Firm* — Toby D. Hain

(57) ABSTRACT

An attenuated total reflection flow cell includes: a source prism; an internal reflection member that produces attenuated reflected light in response to attenuated reflectance of a source light; an exit prism that receives the attenuated reflected light from the internal reflection member; a flow member mechanically coupled to the internal reflection member to provide a flow of fluid to a surface of the internal reflection member.

20 Claims, 27 Drawing Sheets

(A)    2

(B)    2

ATTENUATED TOTAL REFLECTION FLOW CELL

STATEMENT REGARDING FEDERALLY SPONSORED RESEARCH

This invention was made with United States Government support from the National Institute of Standards and Technology. The Government has certain rights in the invention.

BRIEF DESCRIPTION

Disclosed is an attenuated total reflection flow cell comprising: a source prism that provides source light; an internal reflection member mechanically coupled to the source prism and disposed in optical communication with the source prism such that the internal reflection member: receives the source light from the source prism; optically propagates the source light in a plurality of reflections between a first surface of the internal reflection member and a second surface of the internal reflection member; and produces attenuated reflected light in response to attenuated reflectance of the source light at the first surface; an exit prism mechanically coupled to the internal reflection member and disposed in optical communication with the internal reflection member such that the exit prism receives the attenuated reflected light from the internal reflection member; a flow member mechanically coupled to the internal reflection member and disposed in fluid communication with the first surface of the internal reflection member, the flow member comprising: a channel wall disposed in the flow member and opposing the first surface; and a flow channel bounded by the channel wall such that flow channel is interposed between the channel wall and the first surface to provide a fluid in the flow channel so that the fluid contacts the first surface, such that the source light produces an evanescent wave at the first surface that is received by the fluid at the first surface to produce the attenuated reflected light received by the exit prism.

Also disclosed is an attenuated total reflection flow system comprising: the attenuated total reflection flow cell; a first flow line in fluid communication with the flow channel to provide the fluid to the flow channel; a second flow line in fluid communication with the flow channel to receive the fluid from the flow channel; a first mirror to communicate the source light from a light source to the source prism; and a second mirror to receive the attenuated reflected light from the exit prism to a detector.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments is presented herein by way of exemplification and not limitation.

It has been discovered that an attenuated total reflection flow cell herein provides a prism-coupled wafer of material transparent to infrared radiation that provides an easily replaceable internal reflection element for a fluid cell. Advantageously, the wafer can be irreversible altered (e.g., adsorption of molecules thereon) without concern about reconditioning the surface to a pristine state. Prisms that couple infrared radiation into the wafer are reused indefinitely. Inclusion of a temperature-controlled platen provides rigidity required to seal the flow channel to the wafer surface. Unexpectedly, the use of polymeric material to support prisms also provides fine positioning of optical mating surfaces of the prisms to be level with the surface of the platen. Beneficially, this configuration provides localized pressure to be applied to the wafer in an absence of producing a fracture in the wafer.

Figure 1:
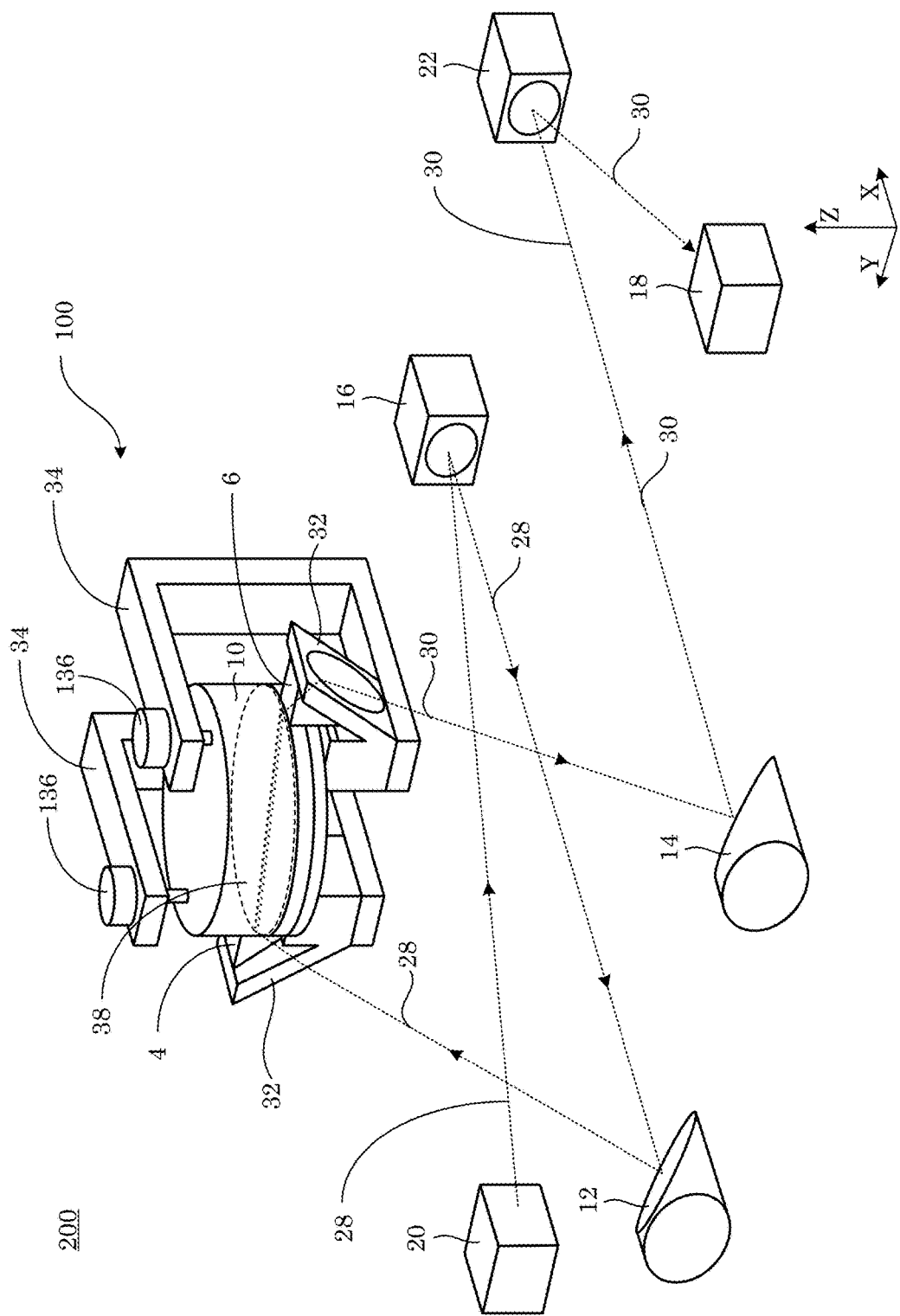
FIG. 1 shows a perspective view of an attenuated total reflection flow system.
Figure 2:
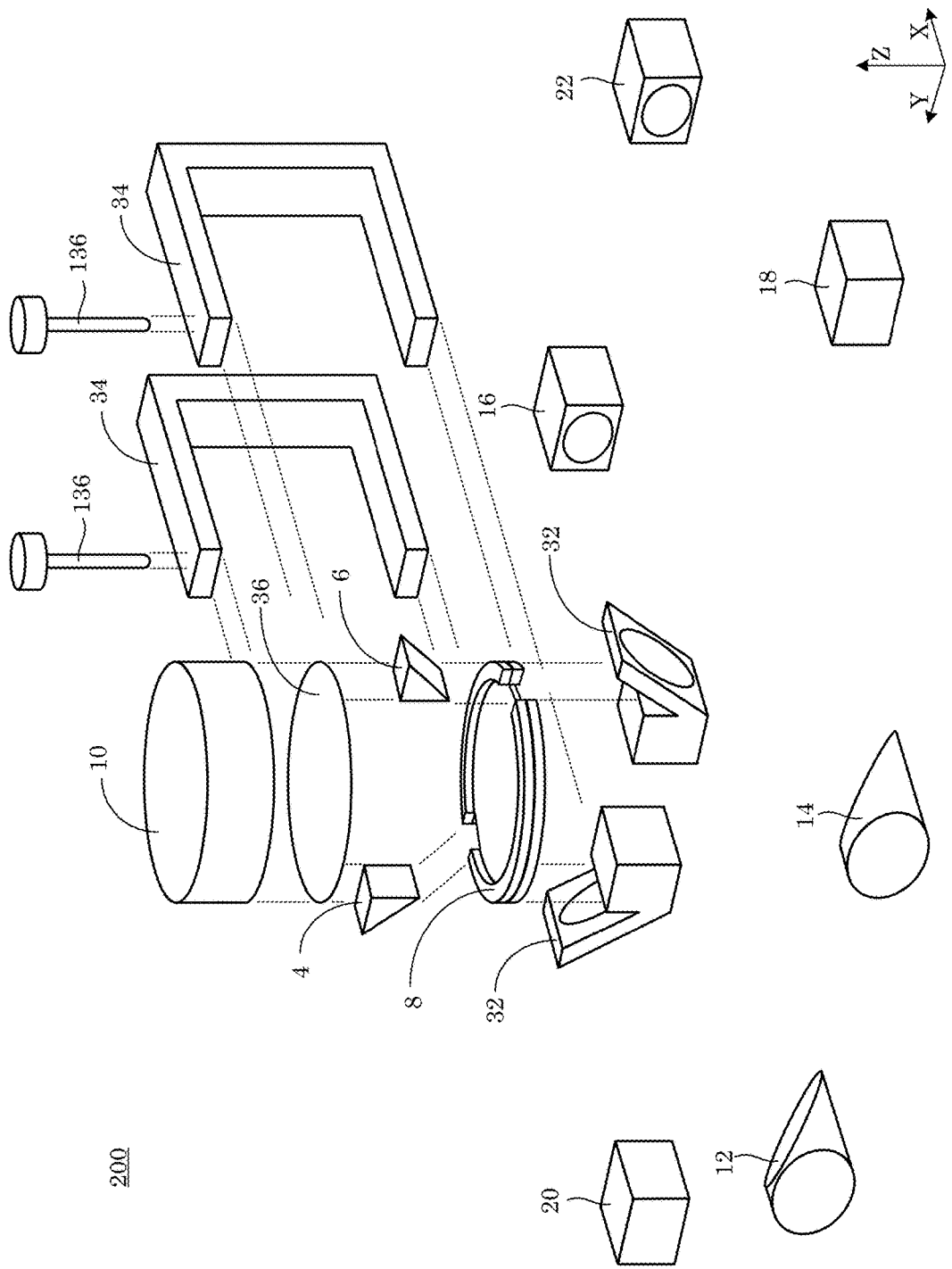
FIG. 2 shows an exploded view of the attenuated total reflection flow system shown in FIG. 1.
Figure 3:
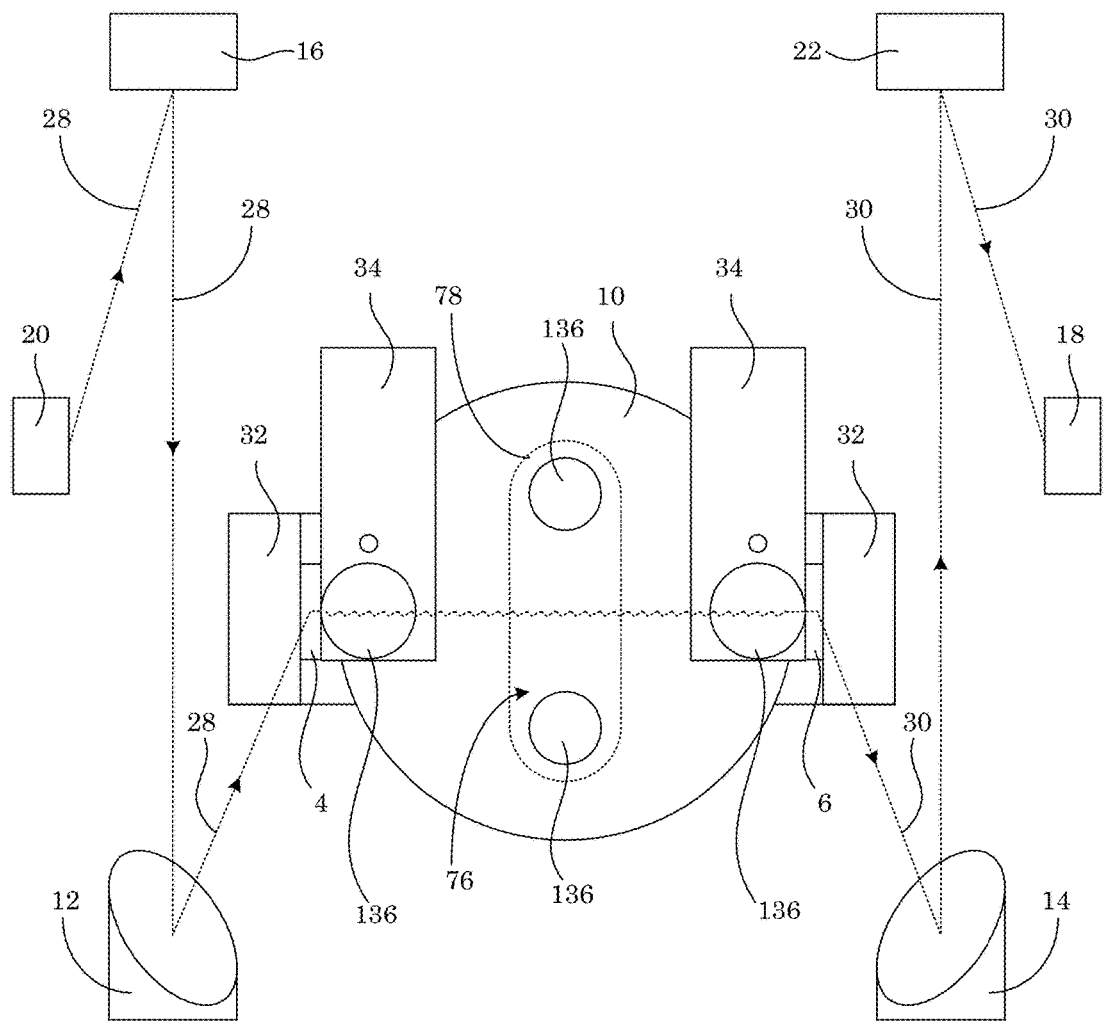
FIG. 3 shows a top view of the attenuated total reflection flow system shown in FIG. 1.
Figure 4:
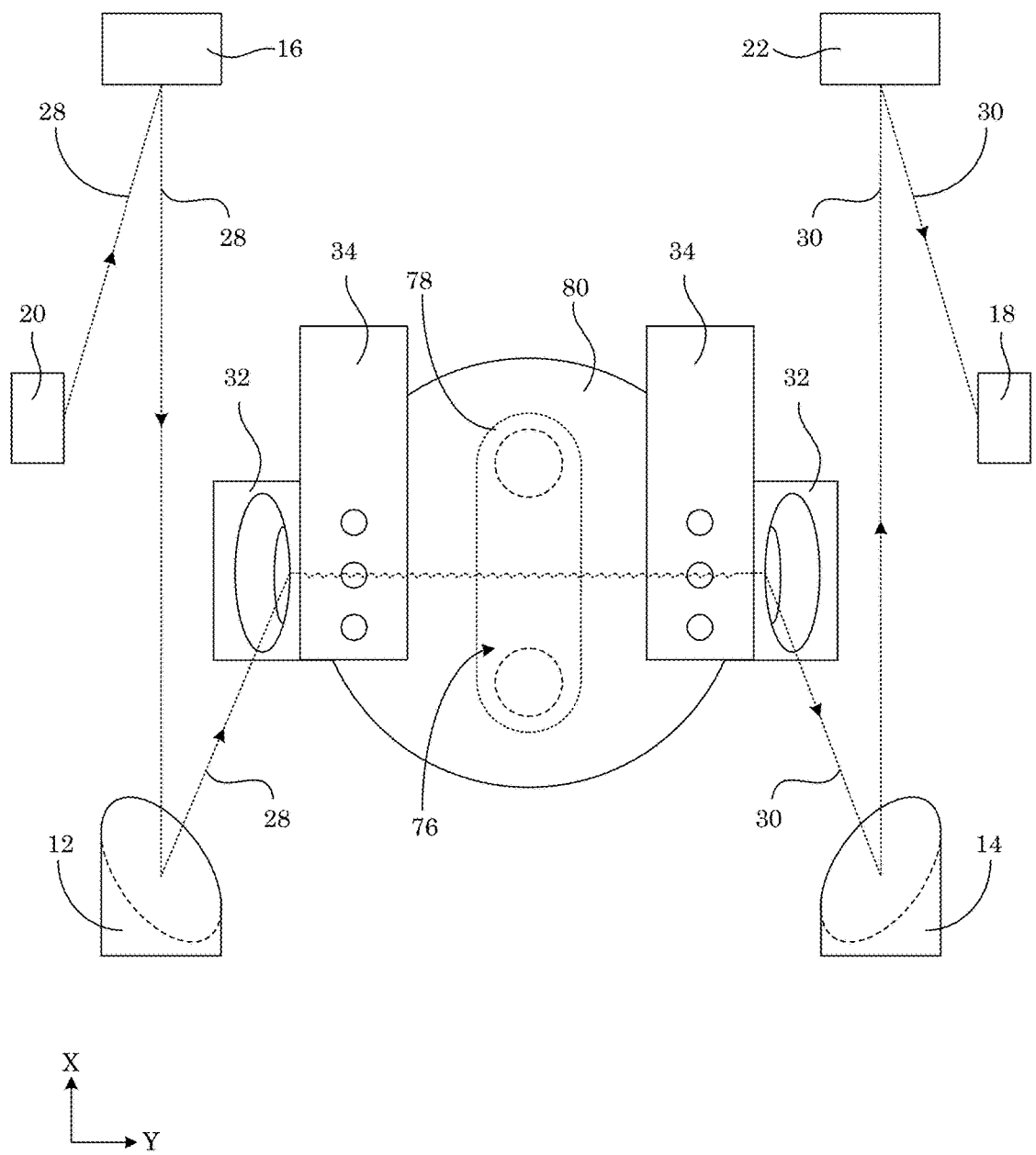
FIG. 4 shows a bottom view of the attenuated total reflection flow system shown in FIG. 1.
Figure 5:
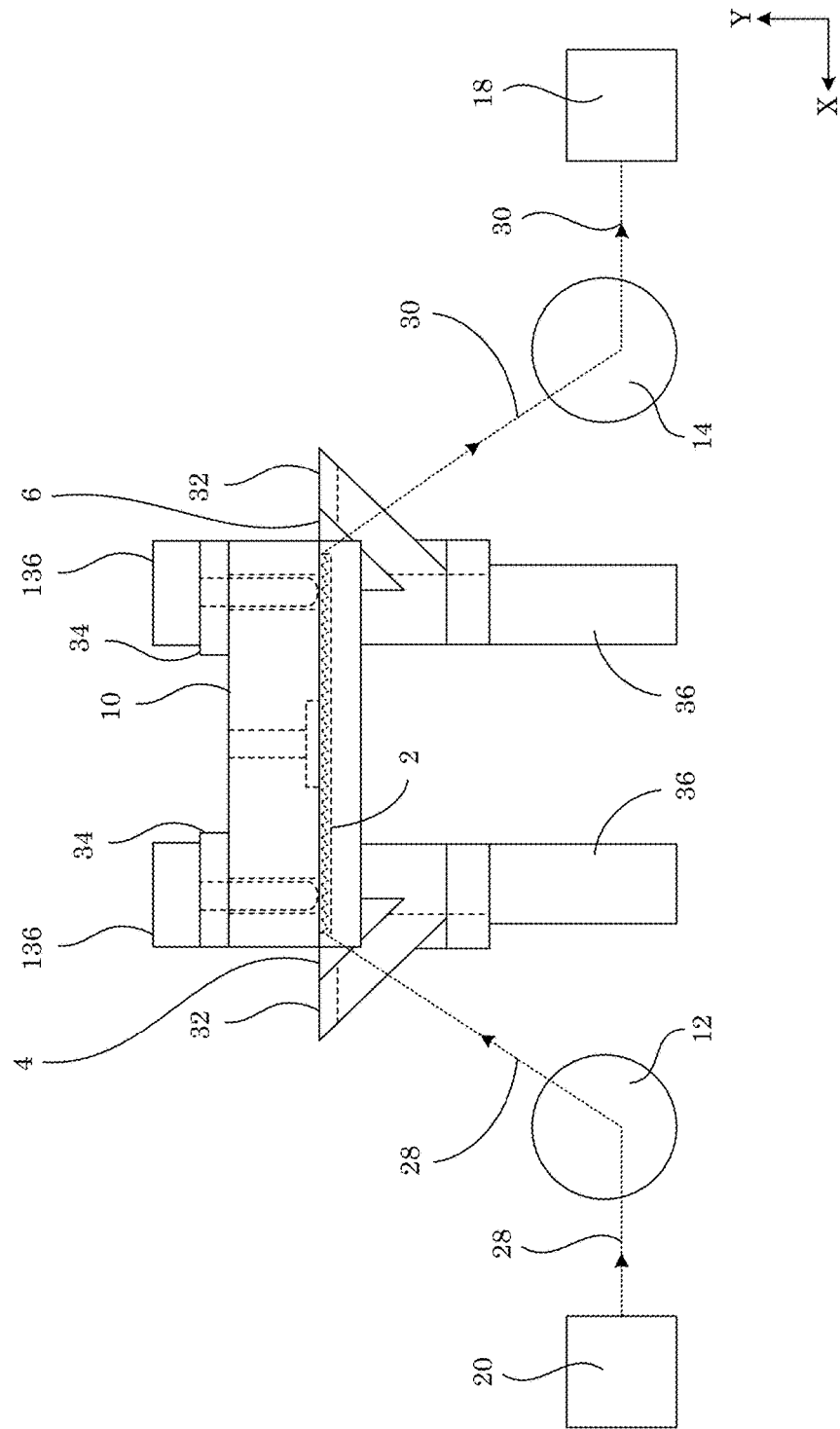
FIG. 5 shows a side view of the attenuated total reflection flow system shown in FIG. 1.

In an embodiment, with reference to FIG. 1 (perspective view), FIG. 2 (exploded view), FIG. 3 (top view), FIG. 4 (bottom view), and FIG. 5 (side view), attenuated total reflection flow system 200 includes attenuated total reflection flow cell 100; first flow line 24 in fluid communication with flow channel 76 that provides fluid to flow channel 76; second flow line 26 in fluid communication with flow channel 76 to receive the fluid from flow channel 76; first mirror 12 to communicate source light 28 from light source 20 to source prism 4; and second mirror 14 to receive attenuated reflected light 30 from exit prism 6 to detector 22. Additional optical components (e.g., a mirror, polarizer, optical filter, lens, and the like) can be included in attenuated total reflection flow system 200 to communicate source light 28 or attenuated reflected light 30, e.g., mirror 16 and mirror 18.

Figure 6:
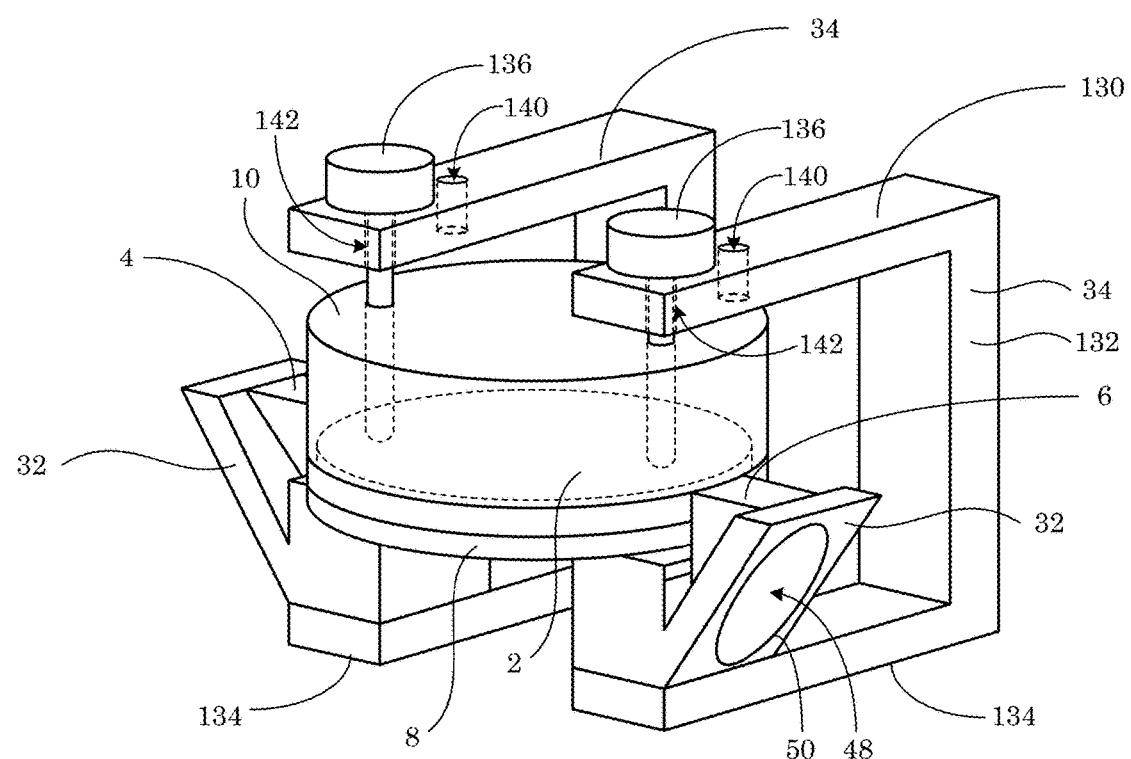
FIG. 6 shows a perspective view of an attenuated total reflection flow cell.
Figure 7:
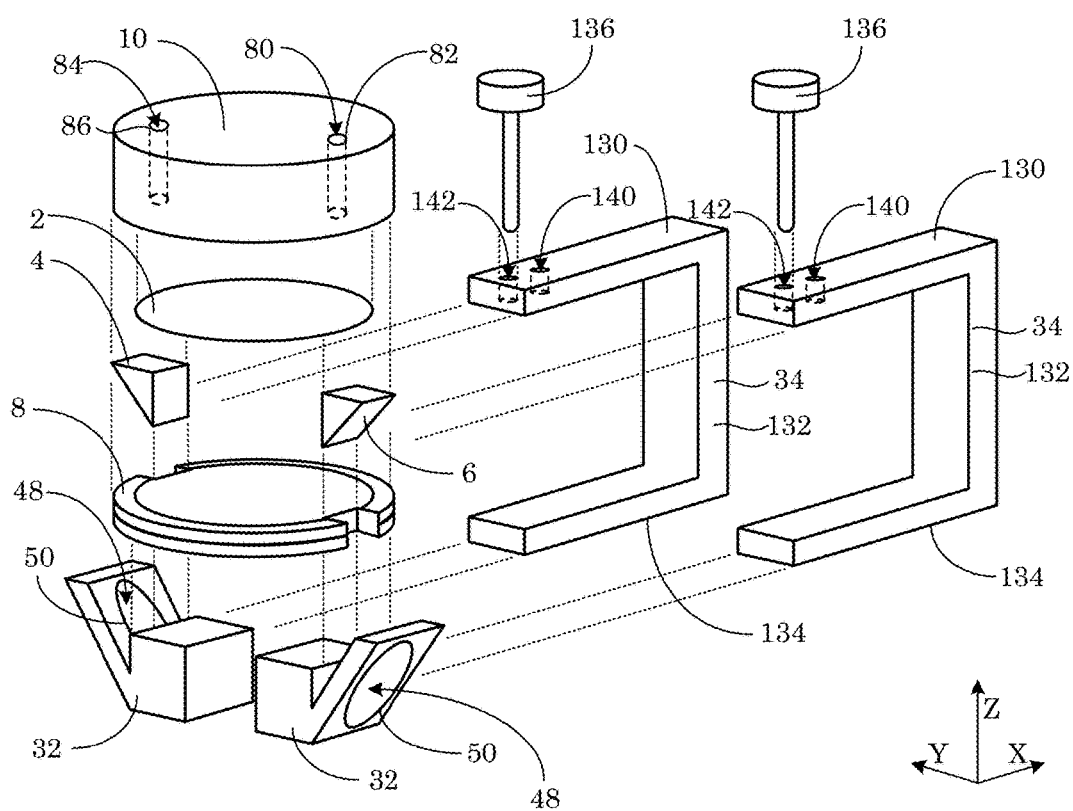
FIG. 7 shows an exploded view of the attenuated total reflection flow cell shown in FIG. 6.
Figure 8:
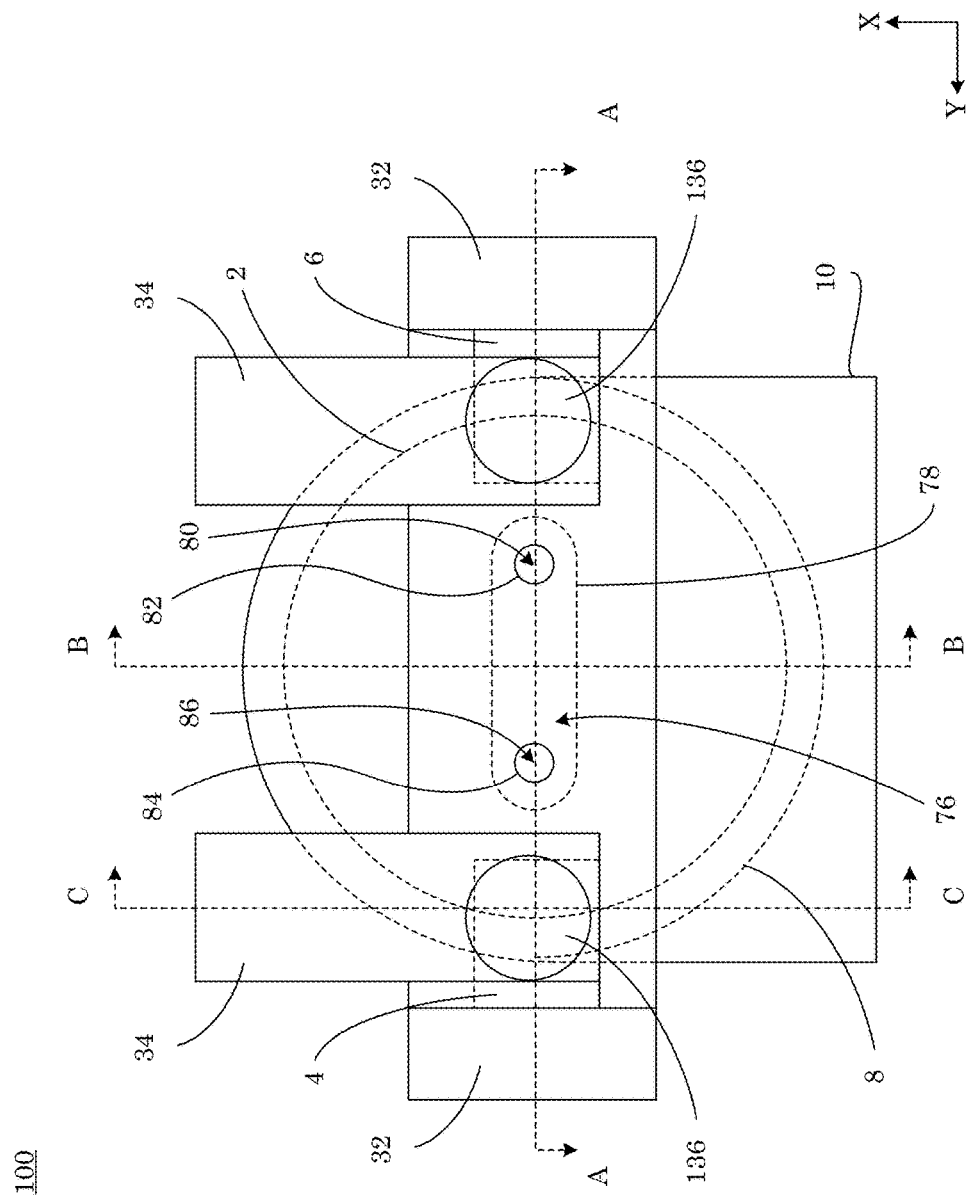
FIG. 8 shows a top view of the attenuated total reflection flow cell shown in FIG. 6.
Figure 9:
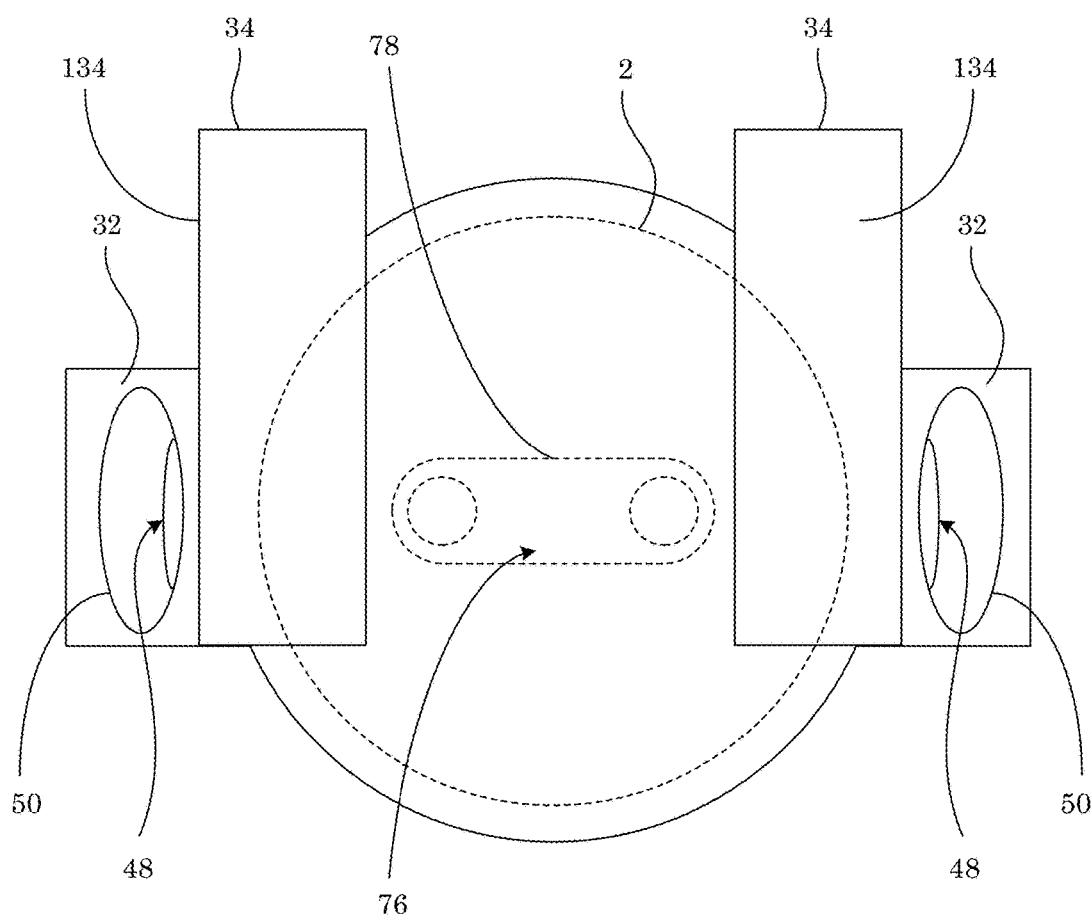
FIG. 9 shows a bottom view of the attenuated total reflection flow cell shown in FIG. 6.
Figure 10:
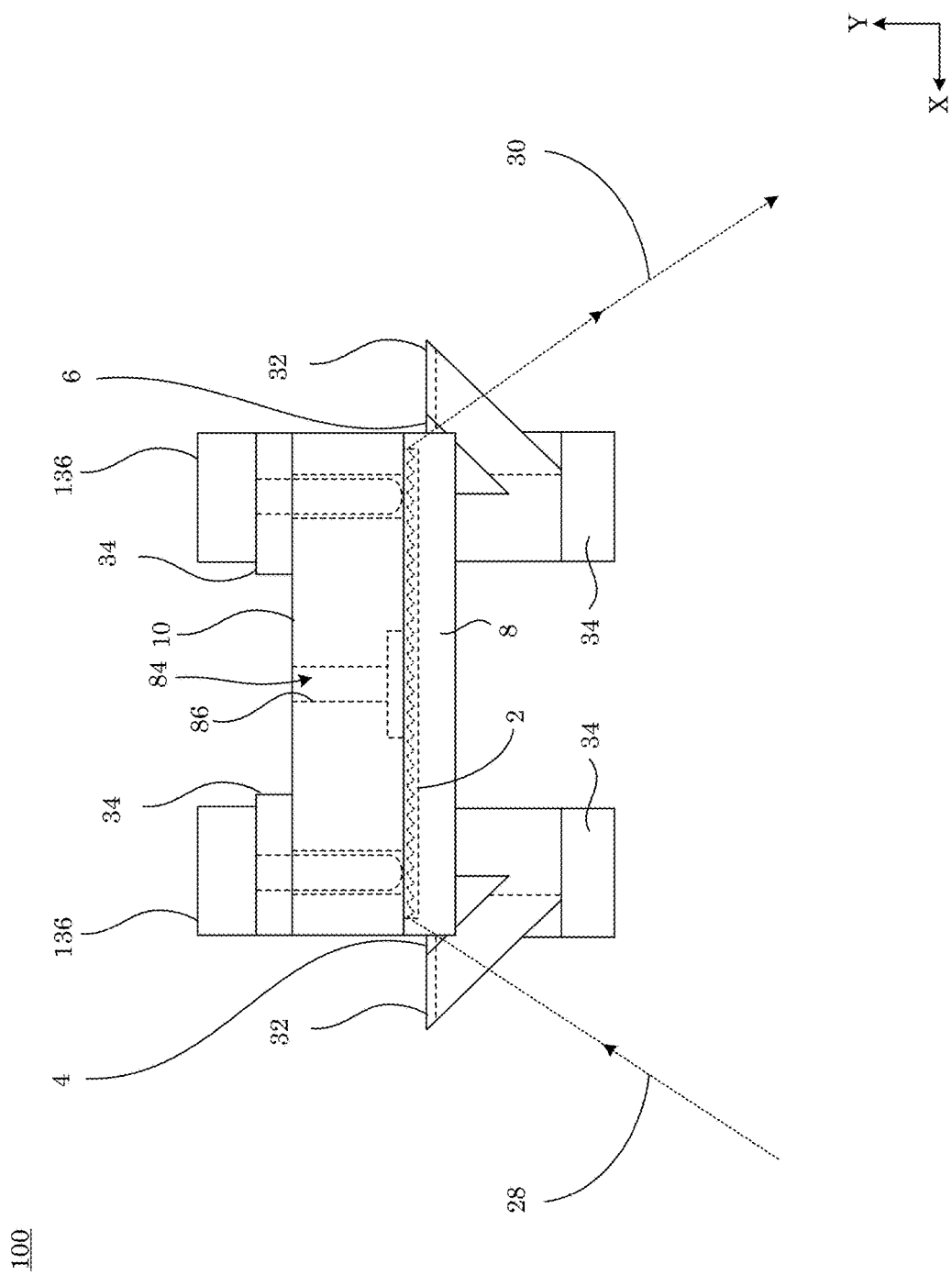
FIG. 10 shows a side view of the attenuated total reflection flow cell shown in FIG. 6.
Figure 11:
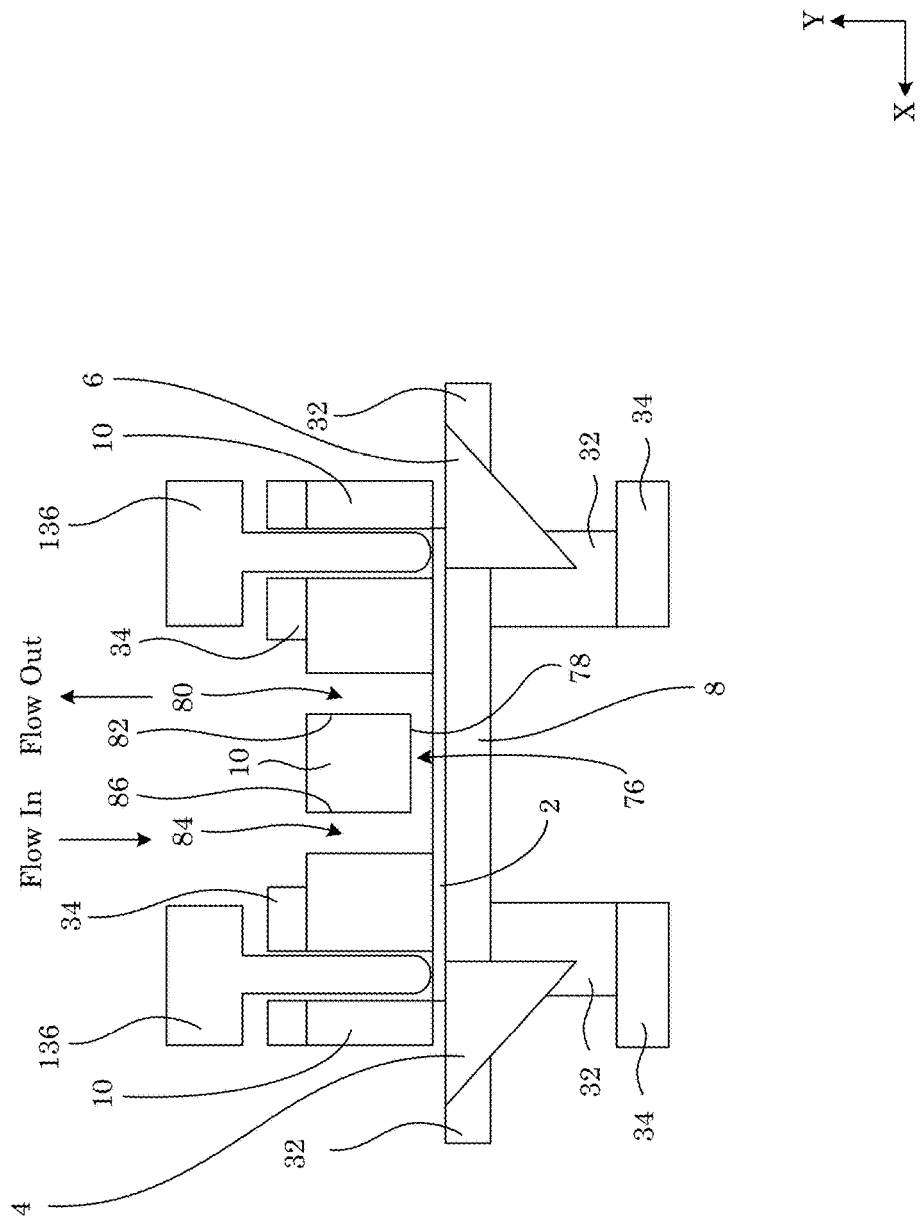
FIG. 11 shows a cross-section along line A-A of the attenuated total reflection flow cell shown in FIG. 8.
Figure 12:
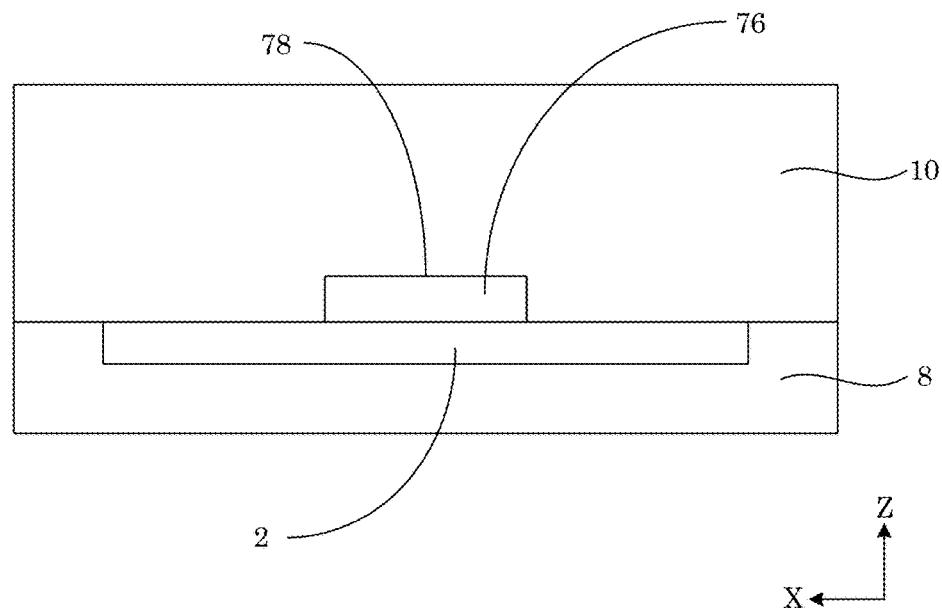
FIG. 12 shows a cross-section along line B-B of the attenuated total reflection flow cell shown in FIG. 8.
Figure 13:
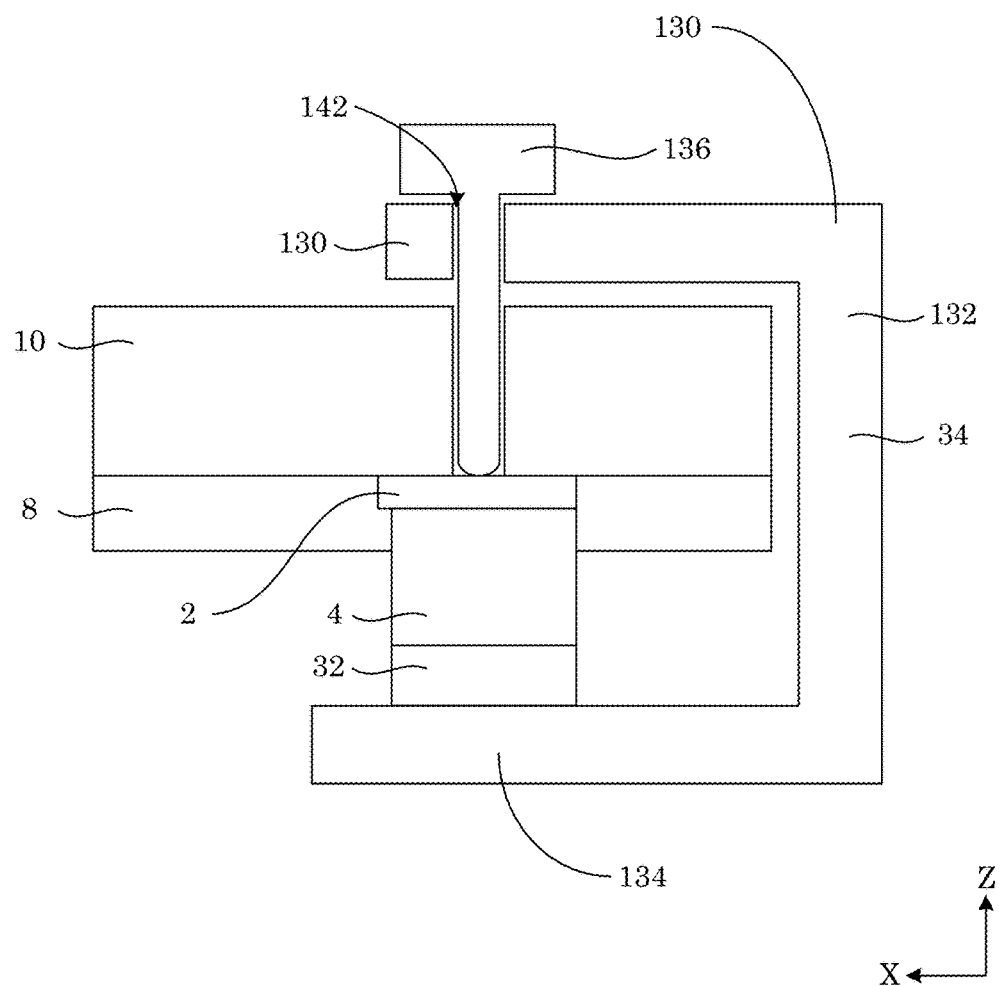
FIG. 13 shows a cross-section along line C-C of the attenuated total reflection flow cell shown in FIG. 8.

In an embodiment, with reference to FIG. 6 (perspective view), FIG. 7 (exploded view), FIG. 8 (top view), FIG. 9 (bottom view), FIG. 10 (side view), FIG. 11 (cross-section along line A-A shown in FIG. 8), FIG. 12 (cross-section along line B-B shown in FIG. 8), and FIG. 13 (cross-section along line C-C shown in FIG. 8), attenuated total reflection flow cell 100 includes source prism 4 that communicates source light 28; internal reflection member 2 mechanically coupled to source prism 4 and disposed in optical communication with source prism 4 such that internal reflection member 2: receives source light 28 from source prism 4, optically propagates source light 28 in a plurality of reflections between first surface 38 of internal reflection member 2 and second surface 40 of internal reflection member 2, and produces attenuated reflected light 30 in response to attenuated reflectance of source light 28 at first surface 38; exit prism 6 mechanically coupled to internal reflection member 2 and disposed in optical communication with internal reflection member 2 such that exit prism 6 receives attenuated reflected light 30 from internal reflection member 2; flow member 10 mechanically coupled to internal reflection member 2 and disposed in fluid communication with first surface 38 of internal reflection member 2, flow member 10 including: channel wall 78 disposed in flow member 10 and opposing first surface 38; and flow channel 76 bounded by channel wall 78 such flow channel 76 is interposed between channel wall 78 and first surface 38 to provide the fluid in flow channel 76 so that the fluid contacts first surface 38, such that source light 28 produces an evanescent wave at first surface 38 that is received by the fluid at first surface 38 to produce attenuated reflected light received by exit prism 30. Here, a direction of flow of the fluid in flow channel 76 is parallel to a direction of propagation of source light 28 in internal reflection member 2.

Figure 14:
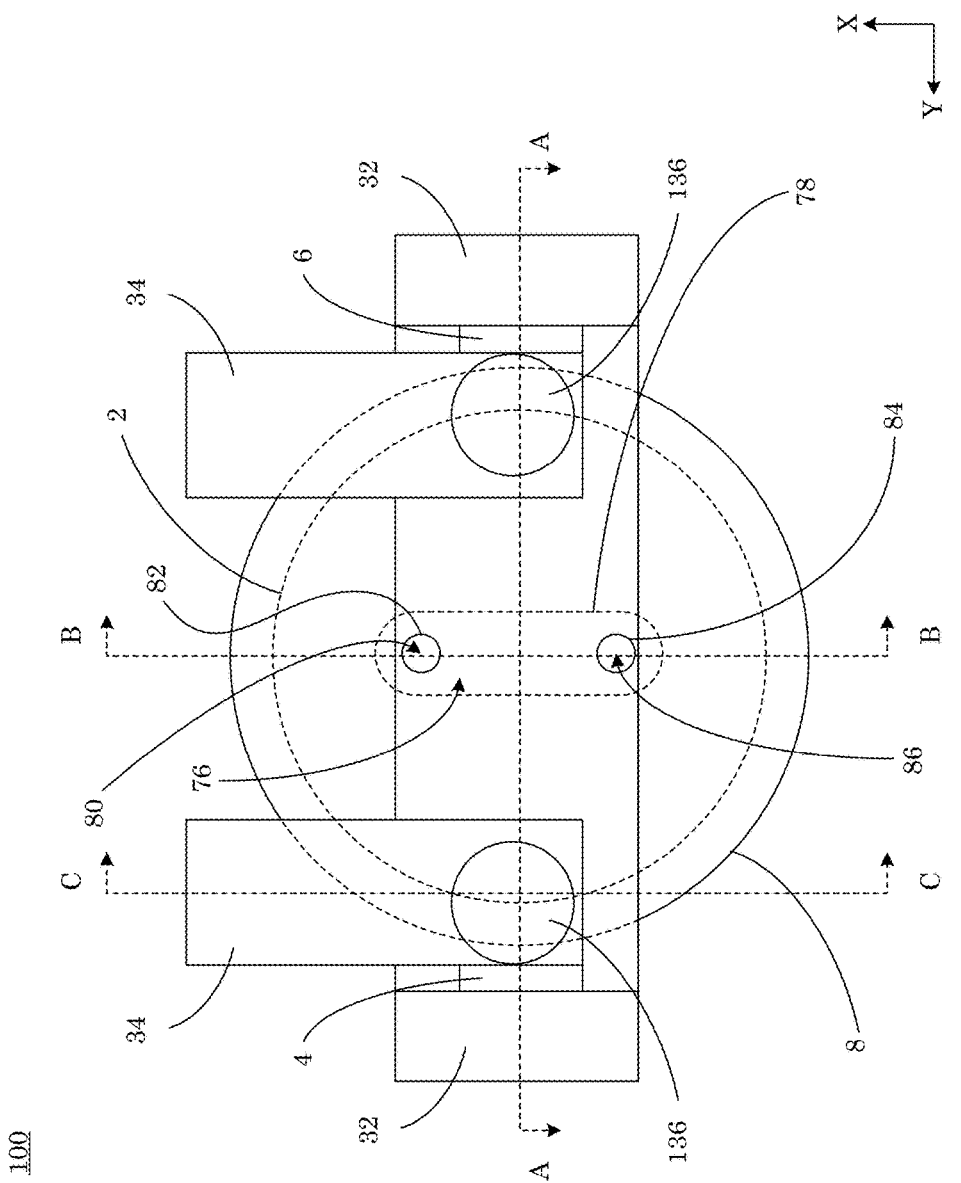
FIG. 14 shows a top view of an attenuated total reflection flow cell.
Figure 15:
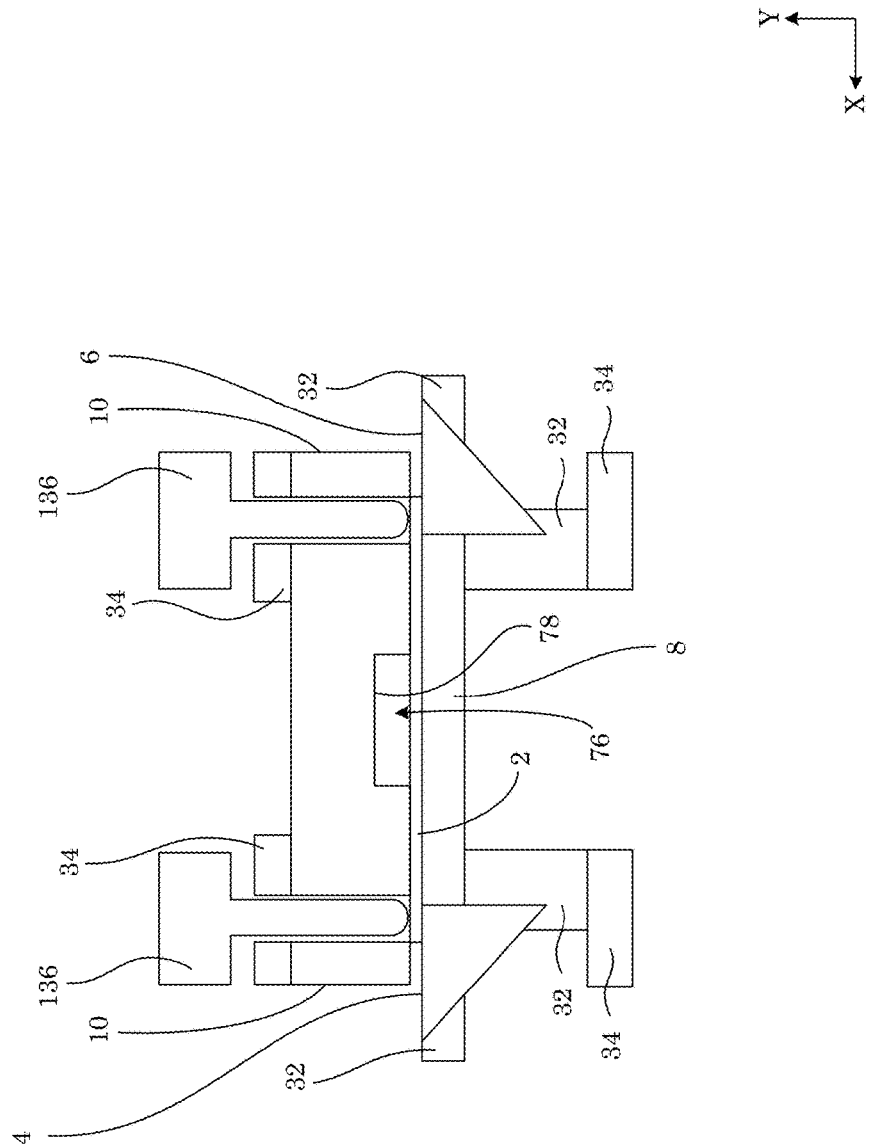
FIG. 15 shows a cross-section along line A-A of the attenuated total reflection flow cell shown in FIG. 14.
Figure 16:
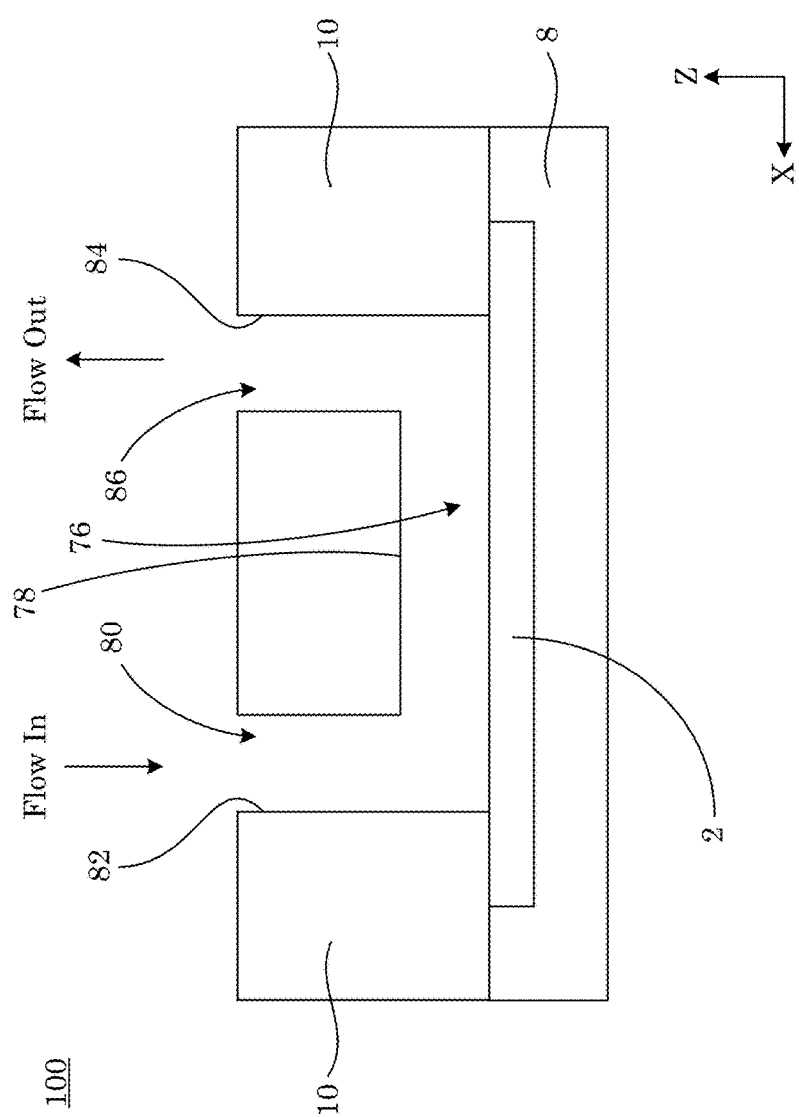
FIG. 16 shows a cross-section along line B-B of the attenuated total reflection flow cell shown in FIG. 14.
Figure 17:
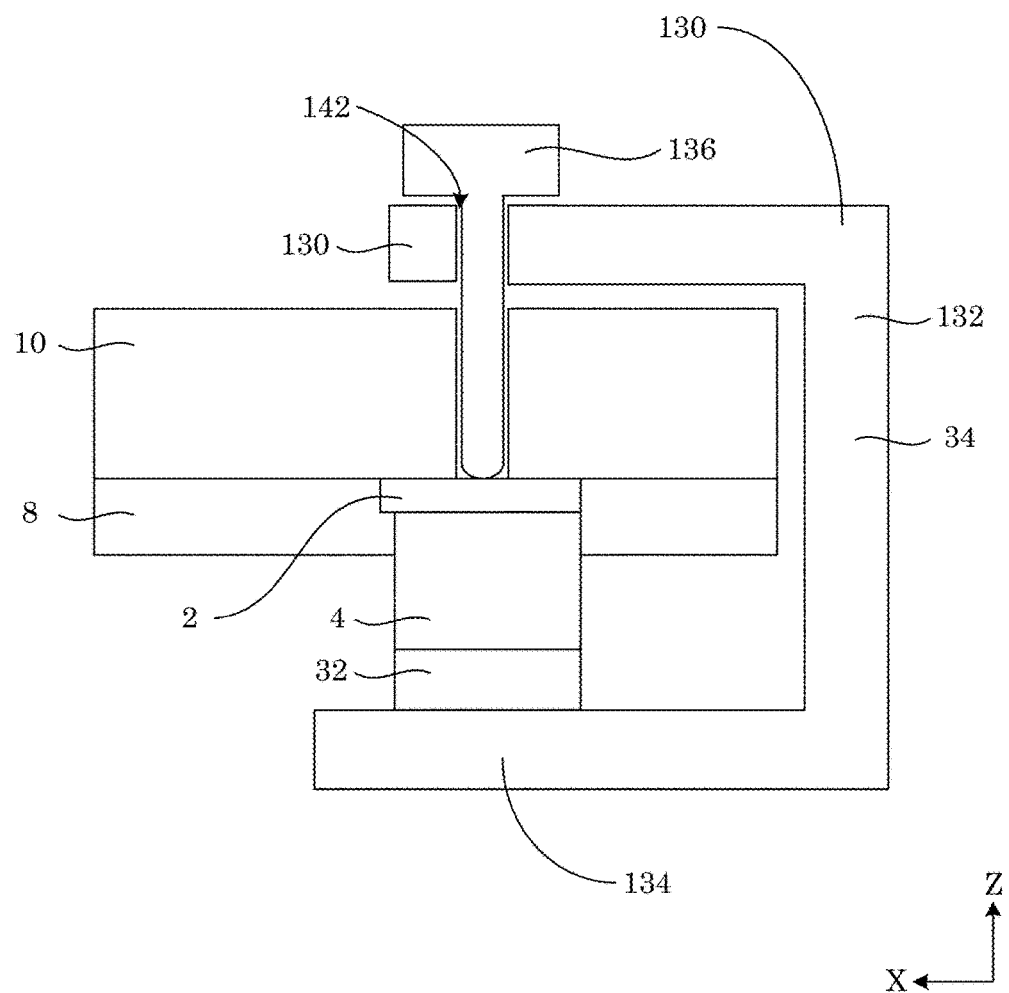
FIG. 17 shows a cross-section along line C-C of the attenuated total reflection flow cell shown in FIG. 14.

It is contemplated that the direction of flow of the fluid in flow channel 76 can be at an arbitrary angle (e.g., from 0° to 90°) to the direction of propagation of source light 28 in internal reflection member 2. The flow may take an arbitrary path in the channels including linear, radial, and serpentine paths. In an embodiment, the direction of flow of the fluid in flow channel 76 is orthogonal to a direction of propagation of source light 28 in internal reflection member 2 from source prism 4 to exit prism 6 as shown in FIG. 14 (top view), FIG. 15 (cross-section along line A-A shown in FIG. 14), FIG. 16 (cross-section along line B-B shown in FIG. 14), and FIG. 17 (cross-section along line C-C shown in FIG. 14). In an embodiment, the direction of flow of the fluid in flow channel 76 is between 0° to 90° to the direction of propagation of source light 28 in internal reflection member 2.

Figure 18:
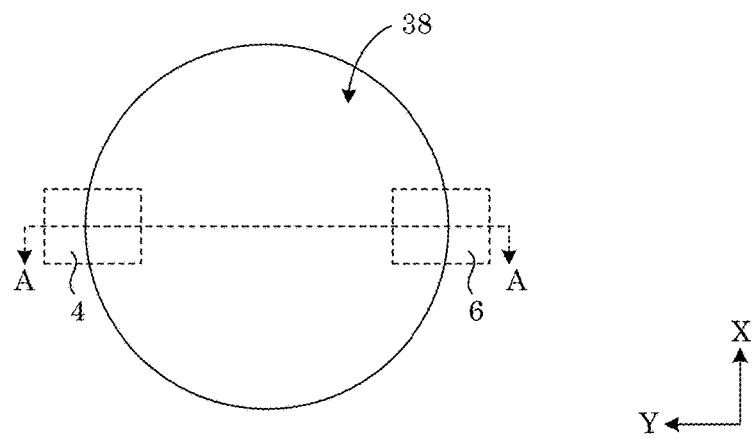
FIG. 18 shows an internal reflection member in which panel A shows a top view, and panel B shows a cross-section along line A-A shown in panel A.
Figure 18:
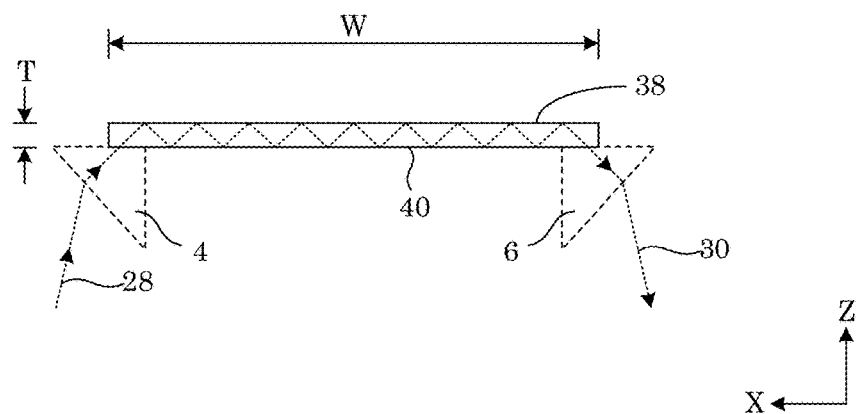

Attenuated total reflection flow cell 100 and articles thereof include internal reflection member 2 that internally reflects source light 28 and produces attenuated reflected light 30 in response to attenuation of source light 28 as source light 28 propagates through internal reflection member 2. Moreover, with reference to FIG. 18 (panel A: top view; panel B cross-section along line A-A shown in panel A), internal reflection member 2 includes first surface 38 in contact with fluid that flows in flow channel 76 of flow member 10. Internal reflection member 2 is transmissive to a wavelength of source light 28 and attenuated reflected light 30. Exemplary internal reflection members 2 include a silicon, germanium, quartz, sapphire, and the like. According to an embodiment, internal reflection member 2 is a semiconductor wafer, e.g., a silicon wafer. First surface 38 can be rough or atomically smooth and flat. Internal reflection member 2 can have thickness T and width W. Width W of internal reflection member 2 can be from 5 micrometers (μm).

According to an embodiment, a thin film is disposed on internal reflection member 2 to provide a solid-phase material that interacts with the fluid through reaction, adsorption, or absorption. Exemplary thin films include metals, oxides, sol-gels, polymers, graphitic materials, MOFs, polymers, and the like. The film can have a thickness from 0.4 nm to 10 μm. In an embodiment, the thin film is unreactive to the fluid and serves to chemically protect the internal reflection member 2. The thin film (e.g., the unreactive coating) can have thicknesses from 0.4 nm to 10 μm. Exemplary thin films include diamond, diamond-like carbon, fluoropolymers, graphene, and the like. In an embodiment, the surface enhanced infrared absorption (SEIRA) phenomenon is used to enhance absorption by adsorbed molecules. Discontinuous thin film of gold, silver, platinum, or other SEIRA-active materials is in disposed on the internal reflection member 2. In an embodiment, the thin film is an electrically conductive layer. The electrically conductive layer can be selected to provide electrical contact with the fluid and can be a material or stack of materials that have high electrical conductivity and advantageously provide a barrier to chemical reaction (e.g., oxidation) with internal reflection member 2. The thin film (e.g., the electrically conductive layer) can have a thicknesses (e.g., from 0.3 nanometers (nm) to 50 nm). In an embodiment, the electrically conductive layer includes a metal (e.g., as well as electrical interconnects thereto, e.g., an electrical interconnect that includes Cu, Au, Ru, Ti, Ta, Al, Ag, a combination thereof, or the like) or a conductive metal oxide (e.g., indium tin oxide). In an embodiment, the internal reflection member 2, thin film, or multiple layers of thin films disposed on internal reflection member 2 is patterned or structured (e.g., through the use of photolithography and etching.) Patterned structures can be used for electrical probes, thermocouples, electrochemical electrodes, and the like. Structures fabricated from the internal reflection member 2 or thin film may include microelectromechanical devices for sensing or actuation in the fluid.

Attenuated total reflection flow cell 100 and articles thereof include prism pad 32 on which prisms (4, 6) are disposed. Prism pads 32 independently comprise a metal, a polymer, a glass, a ceramic, or a combination comprising at least one of the foregoing materials. In an embodiment, prism pad 32 is the polymer and includes a thermoplastic such as polyoxymethylene (POM) (also referred to as acetal, polyacetal polyformaldehyde, and the like in commercially available under trade name DELRIN from DuPont) that provides a selected stiffness (high stiffness), tribology factor (e.g., low friction), and size (e.g., excellent dimensional stability).

Figure 19:
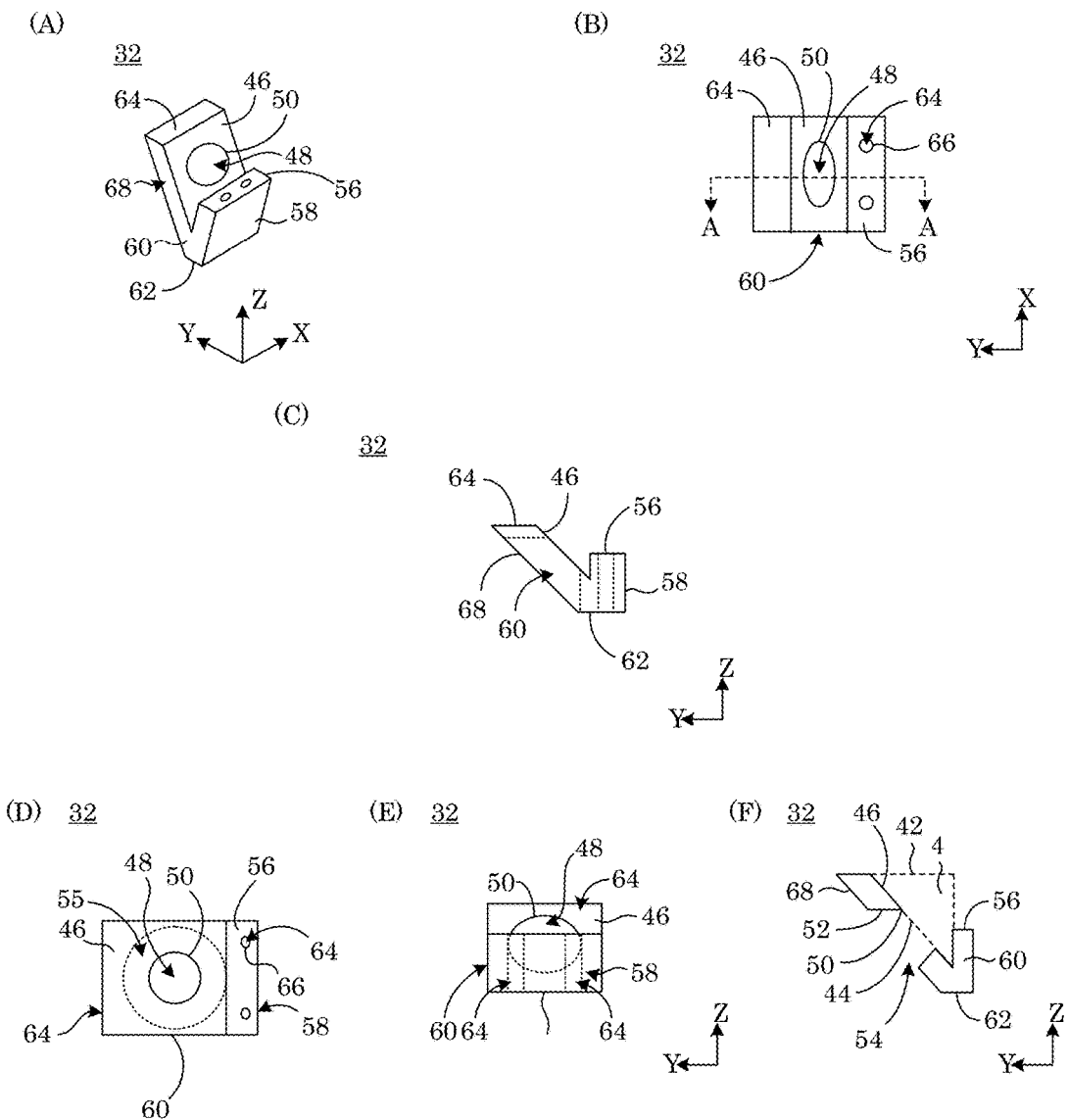
FIG. 19 shows several views of a prism pad in which panel A shows a perspective view; panel B shows a top view; panel C shows a side view; panel D shows a plan view of a mating surface; panel E shows a side view; and panel F shows a cross-section along line A-A shown in panel B.

With reference to FIG. 19, prism pad 32 supports prism (4, 6), wherein optical surface 44 of (4 or 6) contacts meeting surface 46 of prism pad 32. Also, prism pad 32 includes aperture 48 bounded by wall 50 and bevel 52 for optical transmission of light (e.g., source light 28 or attenuated reflected light 30) through aperture 48. Here, source light 28 is communicated through aperture 48 to optical surface 44 of prism 4 such that source light 28 is communicated from optical surface 44 through prism 4 and exits prism 4 at optical surface 42 that is in contact with second surface 40 of internal reflection member 2. Source light 20 is communicated through internal reflection member 2 and attenuated therethrough to produce attenuated reflected light 30 exits at second surface 40 of internal reflection member 2 and received at exit prism 6, specifically at optical surface 42, wherein attenuated reflected light 30 is communicated through exit prism 6 from optical surface 42 to optical surface 44 that is in contact with making service 46 of prism pad 32 such that attenuated reflected light 30 is communicated through aperture 48 of prism pad 32. Additionally, prism pad 32 includes arm 61 bounded by surfaces (56, 58, 60), wherein arm 61 and making service 46 contact and mechanically retain prism (4, 6). Bevel 52 extends from making service 46 to back surface 68 that meets bottom surface 62. Further, bevel 52 provides a large solid angle of view of prism (4 or 6) to transmit light (source light 28 or attenuated reflected light 30, respectively).

Prism pad 32 can be attached to a supporting structure (e.g., an optical bench, spectrometer, and the like) with a fastener (e.g., a screw, bolt, alignment pin, and the like) or bonding material (e.g., an adhesive such as epoxy) and the like. In this regard, prism pad 32 can include holes 64 bounded by wall 66 that extend from surface 56 of arm 61 to bottom surface 62 to fasten present pad 32 to the support structure or to combine present pad 32 to prism (4, 6), internal reflection member 2, flow member 10, and the like. Prism pad 32 can have thickness T (between optical surface 42 and back surface 48 and width W orthogonal thereto that provides support to prism (4, 6).

Figure 20:
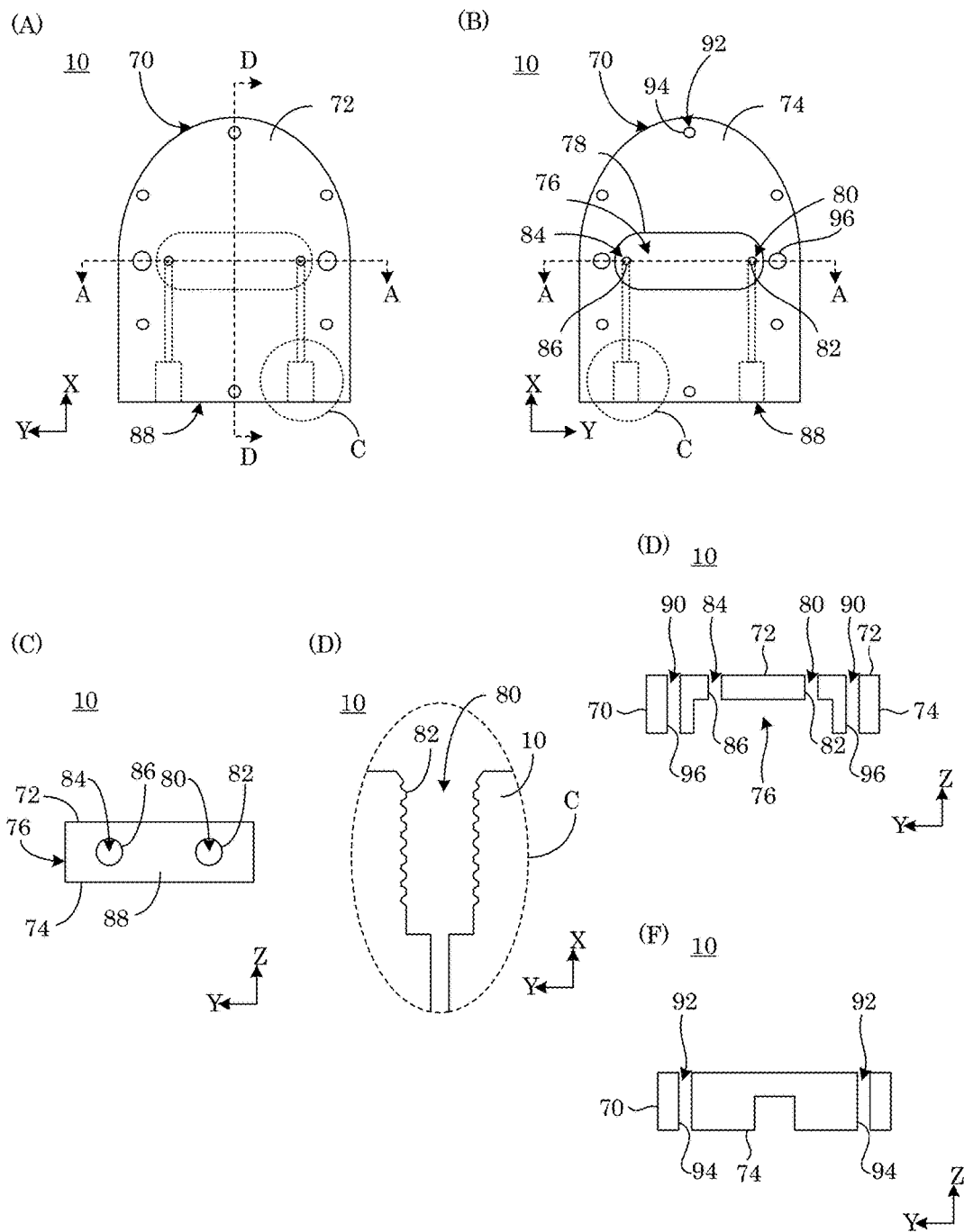
FIG. 20 shows several views of a flow member in which panel A shows a top view; panel B shows a bottom view; panel C shows a side view; panel D shows a zoomed view of portion A shown in panel A; panel E shows a cross-section along line A-A shown in panel A; and panel F shows a cross-section along line D-D shown in panel A.

In an embodiment, with reference to FIG. 20, attenuated total reflection flow cell 100 includes flow member 10. In FIG. 20, panel A shows a top view of flow member 10; panel B shows a bottom view of flow member 10; panel C shows a side view of flow member 10; panel D shows a zoomed view of portion C of flow member 10 shown in panel A; panel E shows a cross-section along line A-A shown in panel A; and panel F shows a cross-section along line D-D shown in panel A. Here, flow member 10 includes flow channel 76 disposed on bottom surface 74 and bordered by channel wall 78 through which the fluid flows. Fluid enters flow channel 76 via fluid port 80 that is bordered by port wall 82, flows through flow channel 76, and exits flow channel 76 through fluid port 84 bordered by port wall 86. Bottom surface 74 is on an opposite surface of flow member 10 with respect to the top surface 72, and sidewall 70 and surface 88 are side surfaces that are interposed in border top surface 72 and bottom surface 74. In this configuration, fluid ports (80, 84) provide fluid communication between flow channel 76 disposed at bottom surface 74 and surface 88 as shown in panel C and zoomed view panel D. As shown in panel D, proximate to surface 88 port wall 82 can include pipe threads to mechanically engage and attach flow line (24, 26) to flow member 10. In this manner, the fluid can be provided from an external source and flowed through flow line (24, 26), fluid ports (80, 84), and flow channel 76.

In an embodiment, flow member 10 includes a plurality of fastener holes 92 bordered by wall 94 to receive a fastener, e.g., a screw, bolt, alignment pin, or the like, to fasten flow member 10 to other components (e.g., platen 8 (shown, e.g., in FIG. 10 and FIG. 21) clamp 34 (shown, e.g., in FIG. 10 and FIG. 22) of attenuated total reflection flow cell 100. Additionally, flow member 10 can include force member hole 90 bounded by wall 96 to receive force member 136 (see, e.g., force member 136 shown in panel A of FIG. 22).

Flow member 10 can be made of a metal, a polymer, a glass, a ceramic, or a combination comprising at least one of the foregoing materials. In an embodiment, flow member 10 is the polymer and includes a thermoplastic such as polytetrafluoroethylene (PTFE) (commercially available under trademark TEFLON) that provides a selected stiffness (high stiffness), tribology factor (e.g., low friction), size (e.g., excellent dimensional stability), chemical stability (e.g., inertness, resistance, and the like).

Flow member 10 can have a thickness (between top surface 72 and bottom surface 74) and width orthogonal thereto that provides support to prism (4, 6).

Bottom surface 74 of flow member 10 opposes first surface 38 of internal reflection member 2. To seal flow member 10 to internal reflection member 2, a seal can be interposed between bottom surface 74 of flow member 10 and first surface 38 of internal reflection member 2. The seal can be a gasket, O-ring, and the like made of an elastomer. The elastomer can be selected to provide chemical compatibility with fluid in flow channel 76. Exemplary elastomers include nitrile rubber, fluoropolymers (commercially available under the trade name VITON from DuPont), perfluoroelastomers (commercially available under the trade name KALREZ from DuPont), silicone rubber, graphite foil, and the like. The seal can be disposed proximate to channel wall 78 and distal to surfaces (70, 88) to constrain the fluid in flow channel 76. A gland (e.g., an O-ring gland) can be formed in bottom surface 74 of flow member 10 to receive the seal.

Figure 21:
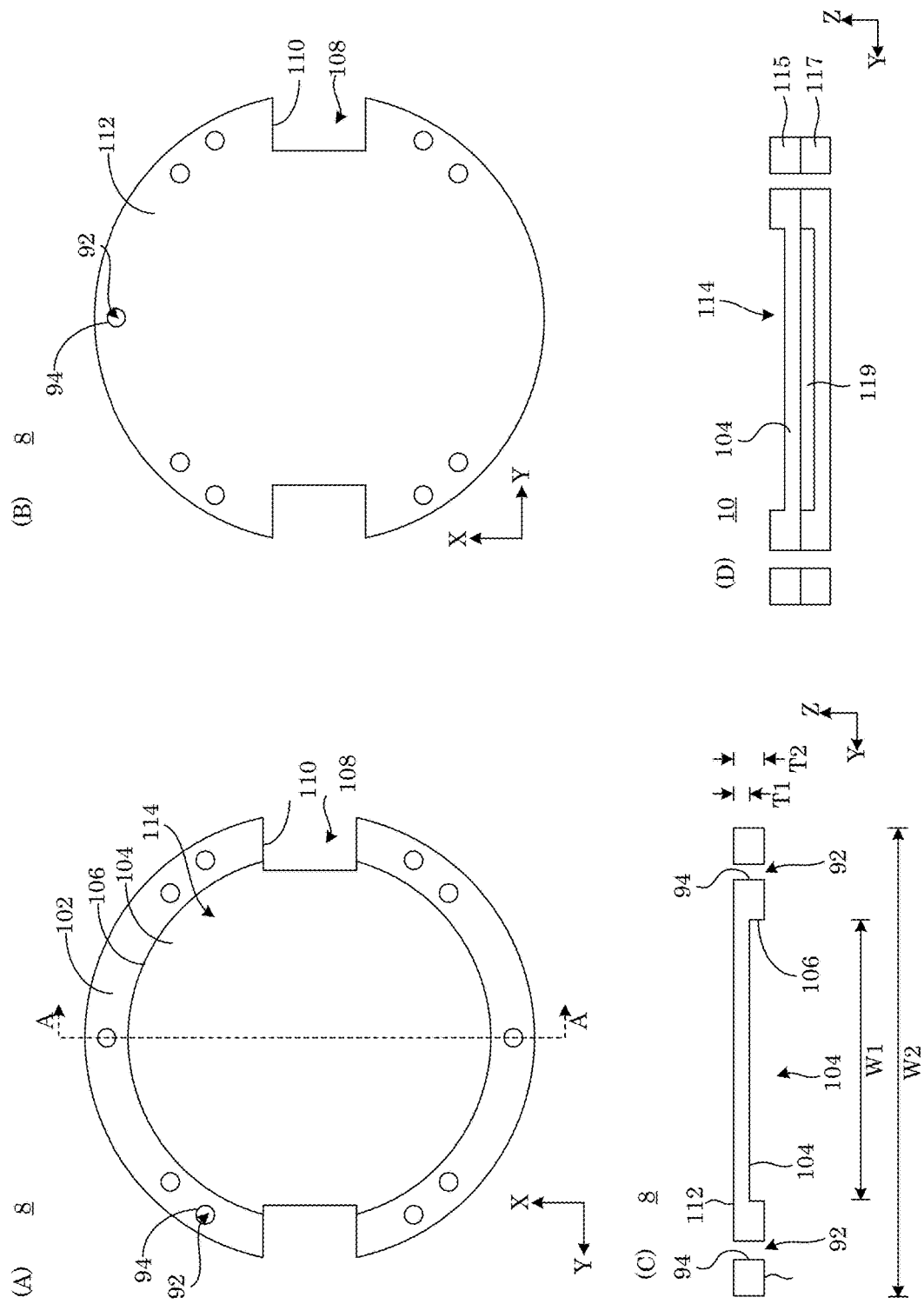
FIG. 21 shows several views of a platen in which panel A shows a top view; panel B shows a bottom view; panel C shows a cross-section along line A-A shown in panel A.

In an embodiment, with reference to FIG. 21, attenuated total reflection flow cell 100 includes platen 8. In FIG. 20, panel A shows a top view of platen 8; panel B shows a bottom view of platen 8, and panel C shows a cross-section along line A-A shown in panel A. Here, platen 8 includes receiver 114 to receive internal reflection member 2 such that internal reflection member 2 is in thermal contact with receiver surface 104. Receiver 114 is recessed in platen 8 and bounded by receiver surface 104 and wall 106. Mating wall 102 engages bottom surface 74 of flow member 10. In this arrangement, second surface 40 of internal reflection member 2 contacts receiver surface 104 of platen 8, and first surface 38 of internal reflection member 2 contacts bottom surface 74 of flow member 10 such that internal reflection member 2 is interposed between bottom surface 74 of flow member 10 and receiver surface 104 of platen 8. Platen 8 also includes aperture 92 bounded by wall 94 to receive a fastener (e.g., a screw). Wall 94 can include threads to engage threads of the fastener to attach flow member 10 to platen 8, wherein the fastener is disposed in fastener hole 92 in flow member 10 and disposed in aperture 92 an engaged by wall 94. Additionally, platen 8 includes recess 108 bounded by wall 110 wherein and do that, wherein recess 108 receives prism (4 or 6).

Platen 8 can be a monolithic structure is shown in panel C of FIG. 21 or can include a plurality of mating structures shown in panel D of FIG. 21. In panel D, flow member 10 includes first portion 115 disposed on second portion 117. Here, first portion 115 include the foregoing features described with regard to panels A, B, and C, and second portion 117 mates with first portion 115 using a fastener or adhesive. Moreover, temperature member 119 can be interposed between first portion 115 and second portion 117 to heat, cool, or maintain a temperature of platen 8. Exemplary temperature members 119 include an electrical device (e.g., a resistive heater, Peltier junction, and the like), liquid flow (e.g., water line, liquid nitrogen line, and the like), electromagnetic susceptor, and the like. Electrical leads for the electrical device of temperature member 119 can protrude from platen 84 to connect to a controller or power supply. Feed lines for the liquid flow (e.g., tubing or the like) temperature is from platen 84 to connect to a liquid supply, valve, and the like. Accordingly, the temperature of platen 8 can be from −269° C. to 1200° C., specifically from −269° C. to 1200° C., and more specifically from −269° C. to 1200° C. It is contemplated that a temperature of internal reflection member 2 can be controlled or maintained via platen 8 using temperature member 119 so that the temperature of internal reflection member 2 can be from −196° C. to 200° C., specifically from −196° C. to 200° C., and more specifically from −196° C. to 200° C.

Platen 8 can be made of a metal, a polymer, a glass, a ceramic, or a combination comprising at least one of the foregoing materials. In an embodiment, platen 8 is the metal and includes aluminum, stainless steel, copper, and the like.

Platen 8 can have a thickness (between making surface 102 and back surface 112) and width orthogonal thereto that provides support to internal reflection member 2 and attachment of flow member 10.

Figure 22:
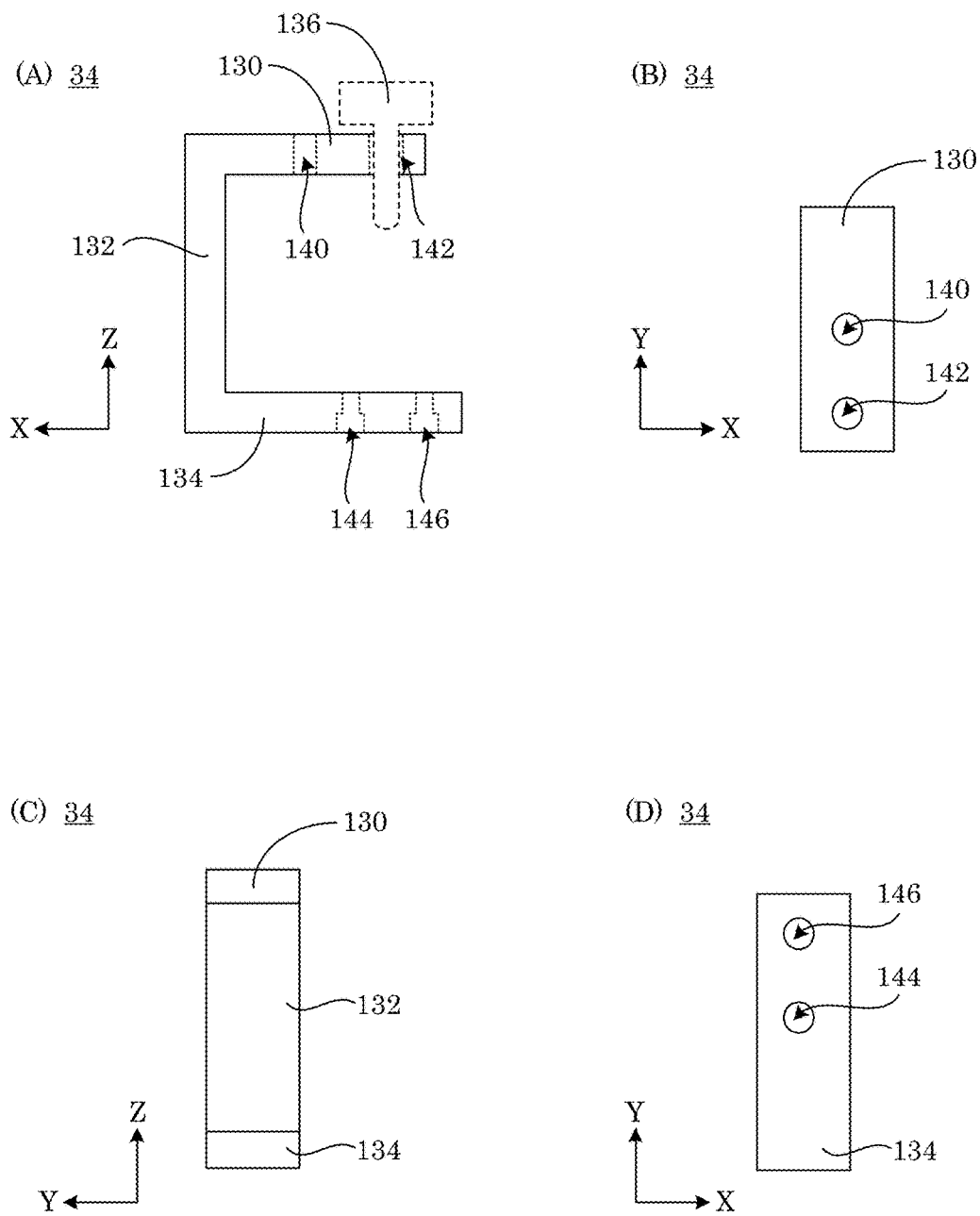
FIG. 22 shows several views of a clamp in which panel A shows a side view; panel B shows a top view; panel C shows a side view; and panel D shows a bottom view.

In an embodiment, with reference to FIG. 22, attenuated total reflection flow cell 100 includes clamp 34. In FIG. 22, panel A shows a side view of a clamp 34; panel B shows a top view of clamp 34, and panel C shows a side view of clamp 34, and panel D shows a bottom view of clamp 34. Here, clamp 34 includes receiver 141 bounded by arms (130, 132, 134). Receiver 141 receives prism pad 32, prism (4 or 6), platen 8, flow member 10 is shown in FIG. 6, FIG. 7, FIG. 8, FIG. 9, and FIG. 10. Here, prism pad 32 is disposed on form 134 of clamp 34. Platen 8 is disposed on arm 61 of prism pad 32, and prism (4 6) is disposed on making service 46 of prism pad 32. Moreover, a portion of internal reflection member 2 is disposed on platen 8, and a portion of internal reflection member 2 is disposed on prism (4 or 6). Flow member 10 is disposed on prisms (4 and 6), internal reflection member 2, and platen 8. Arm 130 of clamp 34 includes holes 140 and 142, wherein a fastener is received in hole 140 to attach clamp 34 two flow member 10. Force member 136 (e.g., a threaded screw with lock nut 141 interposed between head 137 of the threaded screw and arm 130) is disposed in hole 142 and passes through hole 92 of flow member 10 such that terminal end 139 of force member 136 engages top surface 38 of internal reflection member 2. In this manner, forced member 136 provides a compressive force to first surface 38 of internal reflection member 2 against prism (4 or 6) to optically couple internal reflection member 2 and prism (4 or 6) at an interface between second surface 40 of internal reflection member 2 and optical surface 42 of prism (4 or 6). It should be appreciated that the compressive force provided by force member 136 provides the optical coupling between internal reflection member 2 and prisms (4 and 6) in absence of an optical coupling medium such as an immersion oil or optical cement although such optical coupling medium can be present in certain embodiments and interposed between internal reflection member 2 and prisms (4 and 6).

Arm 134 of clamp 34 includes holes (144, 146) to receive and engage a fastener, e.g., to attach clamp 34 to a structural support member so that attenuated total reflection flow cell 100 can be attached to the structural support member such an optical bench or a spectrometer.

Clamp 34 can be made of a metal, a polymer, a glass, a ceramic, or a combination comprising at least one of the foregoing materials. In an embodiment, clamp 34 is the metal and includes aluminum, stainless steel, copper, and the like.

Clamp 34 can have a thickness and width orthogonal thereto of arms (130, 132, 134) that provides support to components disposed in receiver 141.

In an embodiment, a process for making attenuated total reflection flow cell 100 and articles thereof include disposing source prism 4 on first prism pad 32; disposing exit prism 6 on second prism pad 32; disposing platen 8 on prism pads 32; and disposing flow member 10 on platen 8. The process further can include interposing internal reflection member 2 between flow member 10 and platen 8. First prism pad 32 and second prism pad 32 can be attached to a support structure (e.g., optical posts, a spectrometer, and the like). Flow line 24 can be connected to fluid port 80 of flow member 10, and flow line 26 can be connected to fluid port 84.

Attenuated total reflection flow cell 100 and articles thereof have numerous beneficial uses, including acquiring spectroscopic data of the fluid disposed in flow channel 76 of flow member 10. In an embodiment, a process for acquiring spectroscopic data includes providing attenuated total reflection flow cell 100; disposing attenuated total reflection flow cell 100 in a spectrometer to form attenuated total reflection flow system 200; introducing source light 28 from light source 20; introducing fluid into flow channel 76 of flow member 10; communicating source light 28 through source prism 4; receiving source light 28 from source prism 4 at second surface 40 of internal reflection member 2; communicating source light 28 through internal reflection member 2 such that source light 28 internally reflects between first surface 38 and second surface 40 of internal reflection member 2; creating an evanescent wave at first surface 38 from source light 28; contacting first surface 38 of internal reflection member 2 with the fluid in flow channel 76; interacting the evanescent wave at first surface 38 with the fluid in fluid channel 76 that is in contact with first surface 38; producing attenuated reflected light 30 by attenuating source light 28 via interacting the evanescent wave with the fluid in contact with first surface 38; receiving attenuated reflected light 30 from internal reflection member 2 by exit prism 6; communicating attenuated reflected light 30 from exit prism 6; and receiving by detector 22 attenuated reflected light 30 to acquire spectroscopic data of the fluid.

A wavelength of source light 28 can be from 250 nm to 30 μm, specifically from 250 nm to 30 μm, and more specifically from 250 nm to 30 μm. Accordingly, the wavelength of the attenuated reflected light 30 can be from 250 nm to 30 μm, specifically from 250 nm to 30 μm, and more specifically from 250 nm to 30 μm. Exemplary spectroscopic data include infrared data, visible data, ultraviolet data, and the like. The spectroscopic data can be time resolved to monitor dynamic behavior of the fluid in contact with first surface 38 of internal reflection member 2. The dynamic behavior can include chemical reactions, adsorption (chemisorption, physisorption, and the like), thermodynamics, spectroscopic events (e.g., fluorescence, chemiluminescent, and the like), phase changes, isotopic exchange, and the like. In an environment, the wavelength of source light 28 is infrared from 1100 nm to 4000 nm, and the spectroscopic data includes the infrared spectrum of the formation of a reaction product from a reagent in the fluid.

Attenuated total reflection flow cell 100 and articles thereof have numerous advantageous and beneficial properties. A thin internal reflection member 2 permits a greater number of internal reflections within a given length. Because each reflection at the first surface 38 increases the measured absorbance, greater signal-to-noise can be achieved and/or the contact area between the first surface 38 and the fluid can be reduced for a spectroscopic measurement. A thin internal reflection member additionally requires less material and thus reduces the costs of changing the internal reflection member 2 if the prisms 4,6 are reused. The use of prisms 4,6 to couple light into and out of the thin internal reflection member 2 increase optical throughput and reduces the need for fine adjustments of optical components upon changing the internal reflection member compared to coupling into the ends of the thin internal reflection member. Coupling of the flow channel to the internal reflection member allows transients experiments to be performed as well as providing a convenient means to measure an empty cell as a background spectrum. The ease of exchanging the internal reflection member 2 is especially advantageous for measurements requiring irreversible changes to the internal reflection member 2 or to thin films disposed on the member.

The articles and processes herein are illustrated further by the following Example, which is non-limiting.

Example

Attenuated total reflection spectroscopy of analytes.

An attenuated total reflection (ATR) flow cell was made in which a 2-inch undoped Si wafer was used as an internal reflection member (IRM) for ATR. The wafer was mounted onto a custom-built aluminum sample stage that had two germanium right-angle prisms at opposing edges of the wafer to direct the infrared (IR) beam into and out of the wafer. A mid-IR spectrometer provide IR source light. The IR source light beam was directed by a right-angle prism and focused onto a sample stage on which the wafer was exposed by an off-axis parabolic mirror. After the IR light source passed the Ge prism and the IRM on the sample stage to produce attenuated reflected light, the attenuated reflected light was focused by a second off-axis parabolic mirror and directed by a right-angle prism into a liquid nitrogen cooled HgCdTe detector. The flow member of the ATR flow cell was TEFLON and was mounted on top of the wafer (that was coated with ZnO). The flow member in had a fluid port connected to a peristaltic pump by 1/16" tubing. The outlet fluid port for the ATR flow cell was connected to a waste bottle.

A zinc oxide coating was deposited on the silicon wafer. Here, a 2-inch double side polished silicon wafer (having Miller indices <111>, undoped, flow-zone) were subjected to deposition of ZnO thin films using atomic layer deposition (ALD). The Si wafers were placed horizontally in an ALD reactor at 100° C. Pressure during deposition was ~3.5 Torr. Diethyl zinc and deionized water were dosed sequentially to the reactor for 0.2 seconds (s) with 30 s of $N_2$ purging between doses of precursors. A number of ALD cycles was from 100 to 500 for different thicknesses of ZnO thin films on the Si wafers. Growth rate of ALD ZnO was ~1.8 Å/cycle. The silicon wafer that included the ZnO layers was used as the internal reflection member in the attenuated reflection flow cell.

Figure 23:
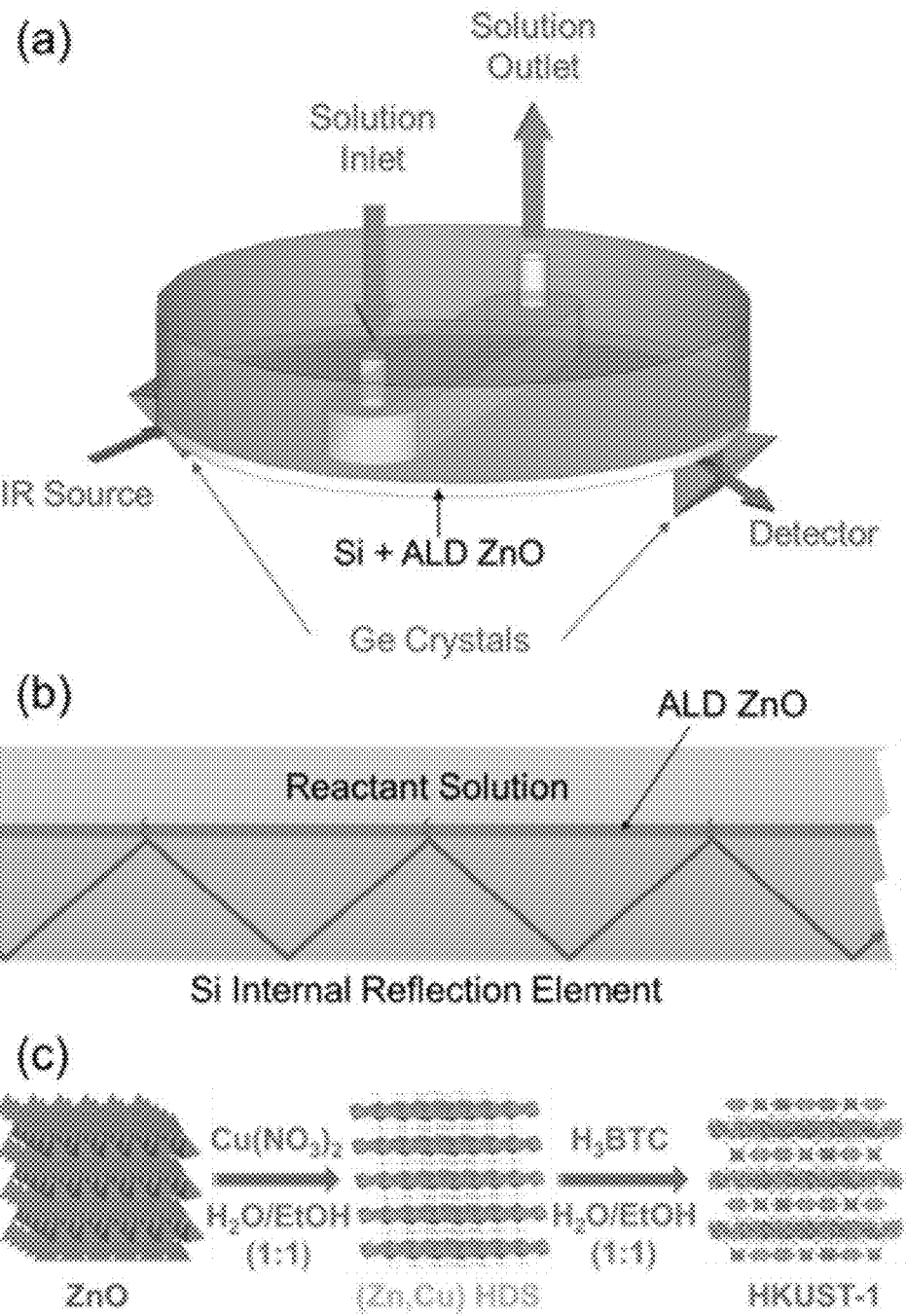
FIG. 23 shows an attenuated total reflection flow cell in panel A arranged to perform FTIR spectroscopy, wherein an undoped silicon wafer is used as an internal reflection member; panel B shows a solid-liquid interface between a first surface of the silicon wafer and a fluid in contact therewith to produce a surface reaction at the first surface to form a metal-organic framework (MOF) in a thin film disposed on the first surface, and panel C shows a layer of ZnO disposed on Si using atomic layer deposition (ALD) for a template to dispose material for rapid room-temperature synthesis of a copper benzene-1,3,5-tricarboxylate MOF (named HKUST-1 from the Hong Kong University of Science and Technology) thin film.

The ATR flow cell included the 2-inch undoped Si wafers as shown in panel A of FIG. 23. The Si wafer was easily replaceable and cheaper than a conventional single crystal internal reflection elements (IRE) that are commercially available for ATR. As above, atomic layer deposition (ALD) was used to deposit the metal oxide thin film ZnO on the Si wafer as a starting material or nucleation layer for metal organic framework (MOF) growth as shown in panel B of FIG. 23. The ATR flow cell disposed in the FTIR spectrometer was used to study the mechanism and kinetics of a reaction route for facile conversion of hydroxy double salt (HDS) to MOF. ZnO reacts with $Cu(NO_3)_2$ solution to form (Zn,Cu) HDS, and an HDS intermediate can convert to a copper benzene-1,3,5-tricarboxylate MOF named for the Hong Kong University of Science and Technology (HKUST-1) at room temperature within 1 minute (min) as shown in panel C of FIG. 23. Here, the ATR flow cell-FTIR captured an in situ dynamics process during formation of HDS and anion exchange in HDS to form the MOF.

We deposited 300 cycles of ALD ZnO (c.a. 54 nm) on the Si wafer as the templating material for HDS. In a typical room-temperature flow synthesis experiment, 300 mM of $Cu(NO_3)_2$ solution in water and ethanol (50:50 v %) was first dosed to the liquid cell for 120 s, followed with a rinse step using the mixed solvent for 60 s. Subsequently, 10 mM of $H_3BTC$ (1,3,5-benzenetricarboxylic acid) solution in water and ethanol (50:50 v %) was then dosed into the cell for 300 s. After the flow of $H_3BTC$ solution, the cell was further rinsed with the mixed solvent for 120 s. We modified the recipe to avoid using DMF in the solvent mixture, as the strong carbonyl peak at ~1680 $cm^{-1}$ may affect the observation of the asymmetric stretching mode for the carboxylate groups in HKUST-1. An FTIR difference spectrum (solvent mixture as the background for processing the spectra) was record every 0.49 s, and the sets of spectra were analyzed by integrating the peaks for $v(NO_3^-)$ at ~1422 $cm^{-1}$, $v(C=C)$ at ~1588 $cm^{-1}$ and $v_{as}(OCO^-)$ at ~1647 $cm^{-1}$. Since the integrated peak area is directly correlated with the concentration of the ligands within the thin films on the Si IRE, we can use the peak area to follow the extent of reaction during HDS formation from ALD ZnO as well as HDS conversion to HKUST-1.

Figure 24:
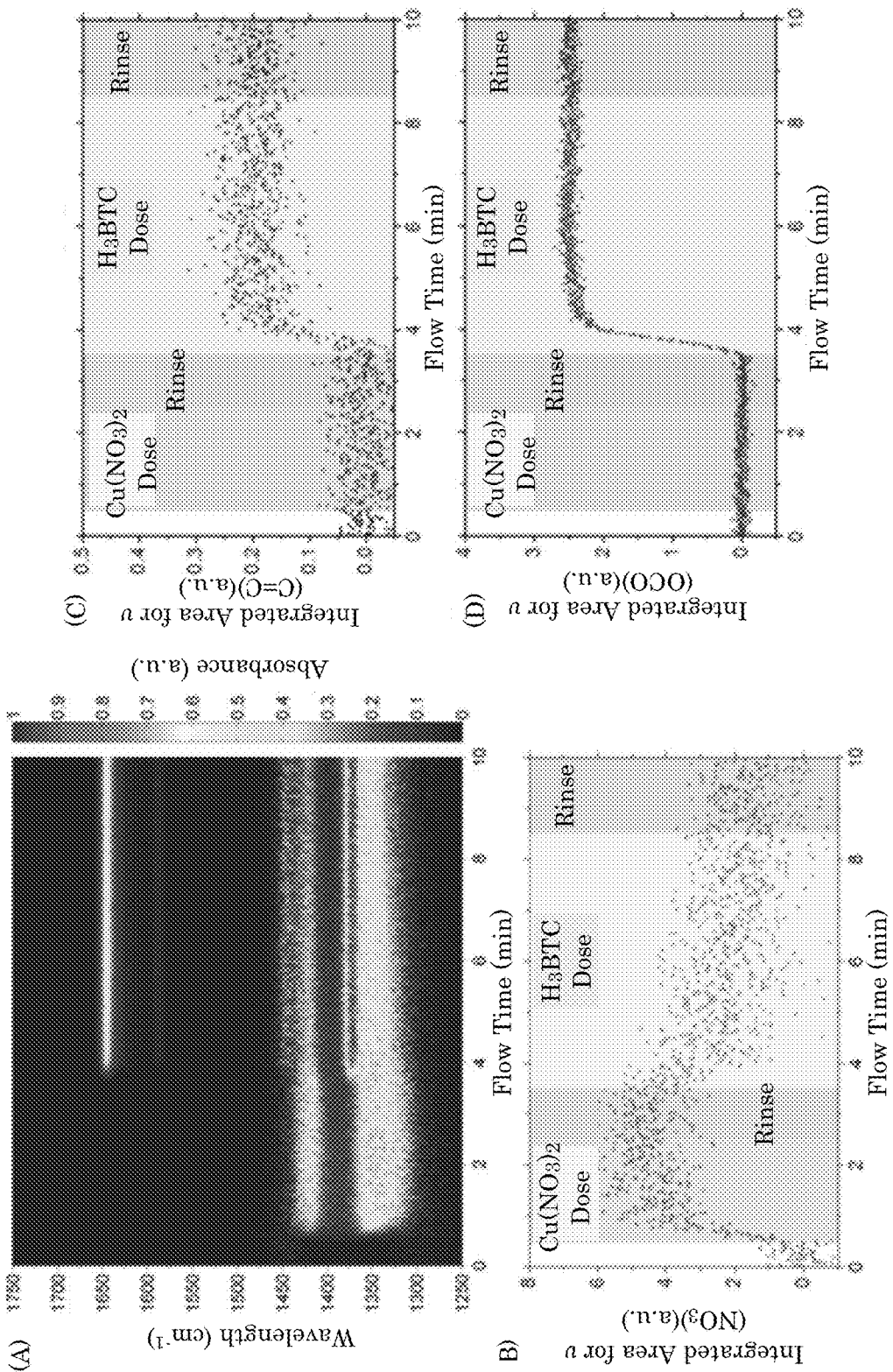
FIG. 24 shows a graph of wavelength versus flow time, and panels B, C, and D show graphs of integrated area versus flow time.

Panel A of FIG. 24 shows time-resolved ATR-FTIR spectra for the surface reactions to form HKUST-1 thin films. Two broad peaks were at 1360 $cm^{-1}$ and 1422 $cm^{-1}$ when the $Cu(NO_3)_2$ solution entered the flow cell. These two peaks were associated with vibrations of the $NO_3^-$ groups within the (Zn,Cu) hydroxy nitrate HDS. As shown in Panel B of FIG. 24, integrated peak area for $v(NO_3^-)$ at ~1422 $cm^{-1}$ increased and reached saturation after 1 min because of formation of (Zn,Cu) HDS from ALD ZnO. After the dose of $Cu(NO_3)_2$ solution, a mixed solvent of water and ethanol (50:50 v %) was introduced into the cell to rinse the surface for 1 min. An intensity of $v(NO_3^-)$ peaks stays unchanged during the rinse step. When the $H_3BTC$ solution was dosed into the flow cell at ~3.5 min, four peaks appear on the spectra as shown in panel A that represented the symmetric and asymmetric stretching modes (1378 $cm^{-1}$ and 1647 $cm^{-1}$, respectively) of the carboxylate groups in HKUST-1, and the C=C vibration modes (1450 $cm^{-1}$ and 1588 $cm^{-1}$) associated with the aromatic ring in the MOF linker. The decreased peak area of $v(NO_3^-)$ and the increased peak area of $v_{as}(OCO^-)$ and $v(C=C)$ were observed simultaneously as shown in panels B, C, and D that was consistent with the anion exchange process for HDS conversion to MOFs. The $v_{as}(OCO^-)$ and $v(C=C)$ peaks reached a maximum area within 1 min that provided a fast rate for forming HKUST-1.

Figure 25:
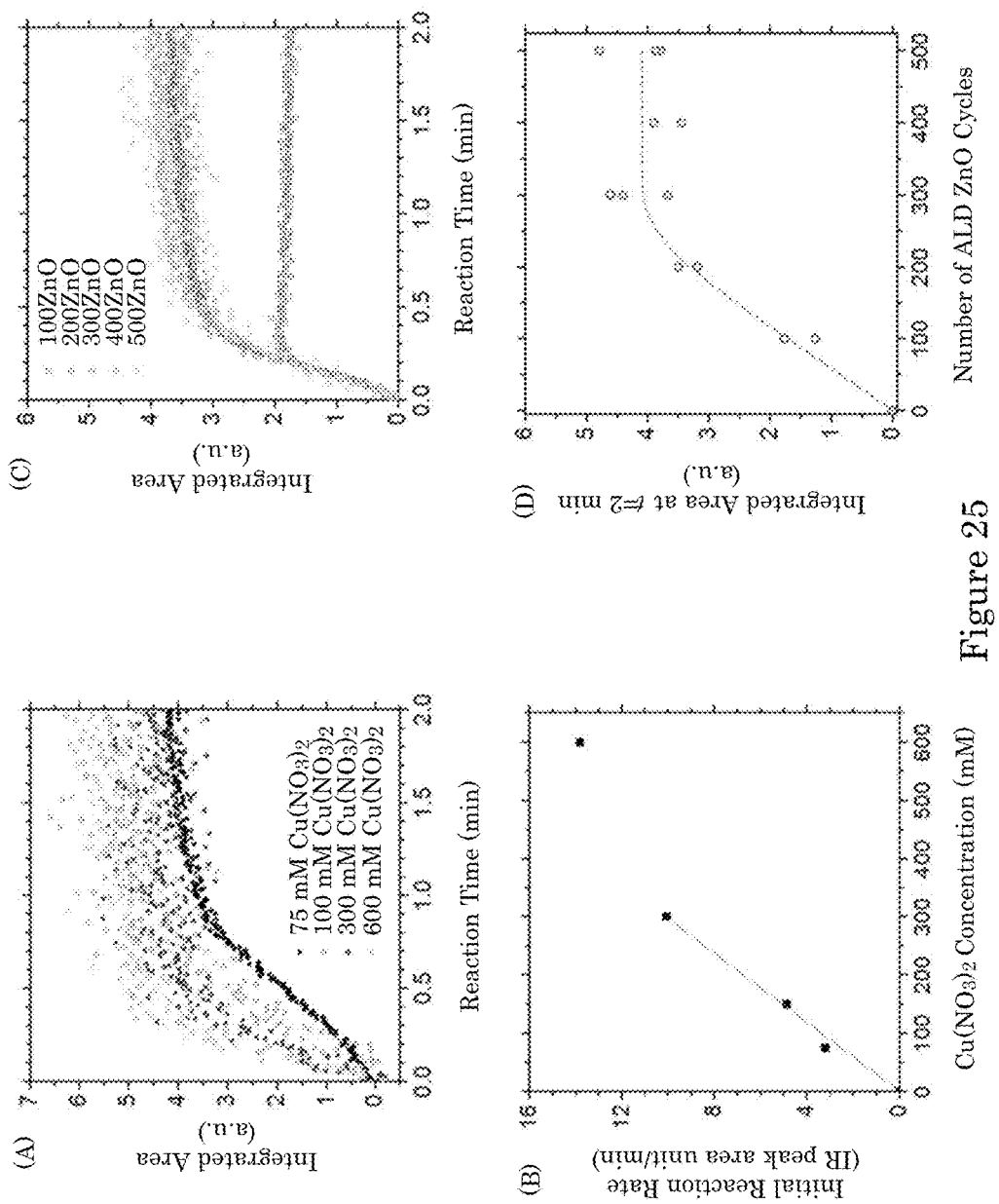
FIG. 25 shows graphs of integrated area versus flow time in panels A, C, and D, and panel B shows a graph of initial reaction rate versus concentration of copper nitrate.

Kinetics for the formation of HDS from ZnO and the conversion of HDS to HKUST-1 were studied. Panel A of FIG. 25 shows the change of integrated IR peak area for $v(NO_3^-)$ at ~1422 $cm^{-1}$ as a function of reaction time when ALD ZnO thin films (300 cycles) reacted with different concentration of $Cu(NO_3)_2$ solutions. For all the concentration tested for the first reaction, $v(NO_3^-)$ signal increase in 1 min and saturated when reaction terminated. The slope of the curves within the first 0.3 min provided an indication of initial reaction rate. Panel B of FIG. 25 shows the initial reaction rate for forming HDS from ZnO increase linearly with $Cu(NO_3)_2$ concentration when the concentration was less than 300 millimolar (mM). At this concentration, the reaction followed first order kinetics. The linear fitting of the initial reaction rate for $c[Cu(NO_3)_2] \leq 300$ mM provided a rate constant $k_{app}$=33.8 (IR Peak Area·$min^{-1}$·$L·mol^{-1}$). At a high concentration (600 mM), $Cu(NO_3)_2$ was in excess, and the reaction rate was not a first-order reaction.

An effect of the thickness of ALD ZnO films on the kinetics of HDS formation was studied. Panel C of FIG. 25 shows integrated $v(NO_3^-)$ peak area during the flow of 300 mM $Cu(NO_3)_2$ solutions on different thickness of ALD ZnO layers (100~500 cycles). Initial reaction rates were almost the same for all the ZnO films. The final integrated $v(NO_3^-)$ peak area at t=2 min was plotted as a function of the number of ALD ZnO cycles deposited on the Si internal reflection member and as shown in Panel D of FIG. 25. Surprisingly, data points for ZnO films thicker than 300 cycles do not follow the linear increase trend for thin ZnO films. We calculated the penetration depth ($d_p$) of the ATR evanescent wave and compared with the film thickness measured from cross sectional SEM images. For the first reaction to form (Zn,Cu) HDS from ZnO, $d_p$ ranges from 0.62 μm to 0.88 μm for the IR wavenumbers of interest (1250~1750 $cm^{-1}$). These $d_p$ values were larger than the thickest film (0.56 μm) converted from 500 cycles of ALD ZnO layer (c.a. 92 nm), confirming that the surface changes during the first reaction for within the detection limit for the ATR setup. Transmission IR measurements and X-ray diffraction patterns also indicated that the film thicknesses of the HDS converted from thick ZnO layers (≥300 cycles) are indeed very similar.

The partial conversion of thick ZnO layers to (Zn,Cu) HDS was possibly a result of diffusion-limited process. As shown in panel C of FIG. 25, the growth rate of HDS from 200~500 cycles of ZnO decreased after 0.5 min. The dense HDS formed on the surface likely to block the reactant from diffusing into the film and could have hindered mass transport process (see FIG. 26). Consequently, the growth of HDS stopped at a certain depth where the reactant was depleted, and an interfacial layer of ZnO was present between the HDS film and the Si substrate. The maximum thickness of the HDS films converted from planar ZnO layers was ~0.5 μm on average.

Figure 26:
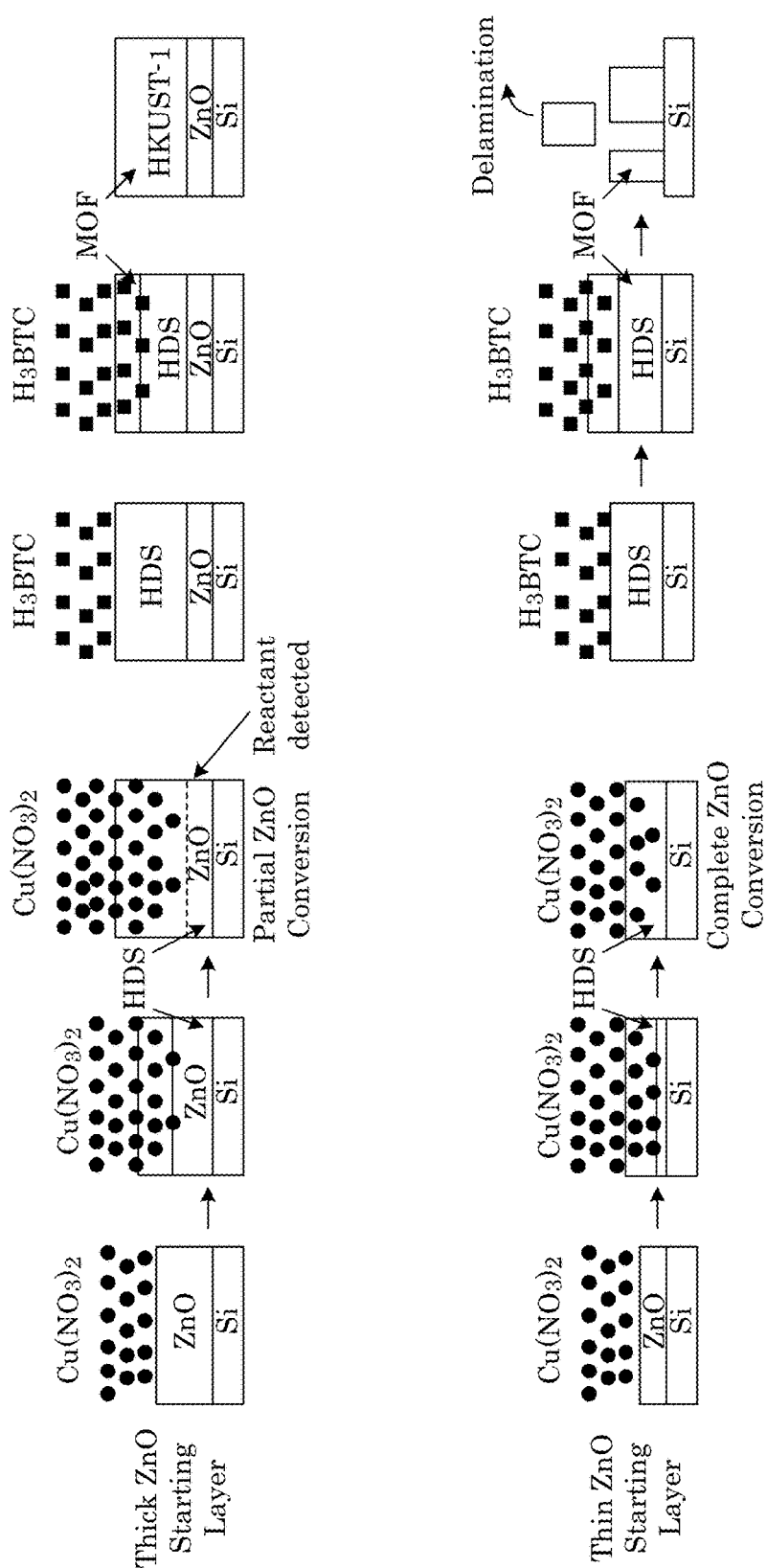
FIG. 26 shows an exemplary reaction and diffusion reagents involved in forming an HKUST-1 thin film.

The ZnO interfacial layer due to partial conversion was involved disposing the MOF thin films on the internal reflection member during conversion of as-synthesized (Zn, Cu) HDS to HKUST-1 films (see FIG. 26). Here, 10 mM of $H_3BTC$ in water/ethanol mixed solvent was dosed into the flow cell, after the flow of $Cu(NO_3)_2$ solution and a rinsing step. With the presence of ZnO interfacial layer, dense and uniform HKUST-1 films were obtained and adhered to the substrate. In comparison, delamination of the MOF layer occurred when HDS was fully consumed in an absence of the ZnO interfacial layer.

Figure 27:
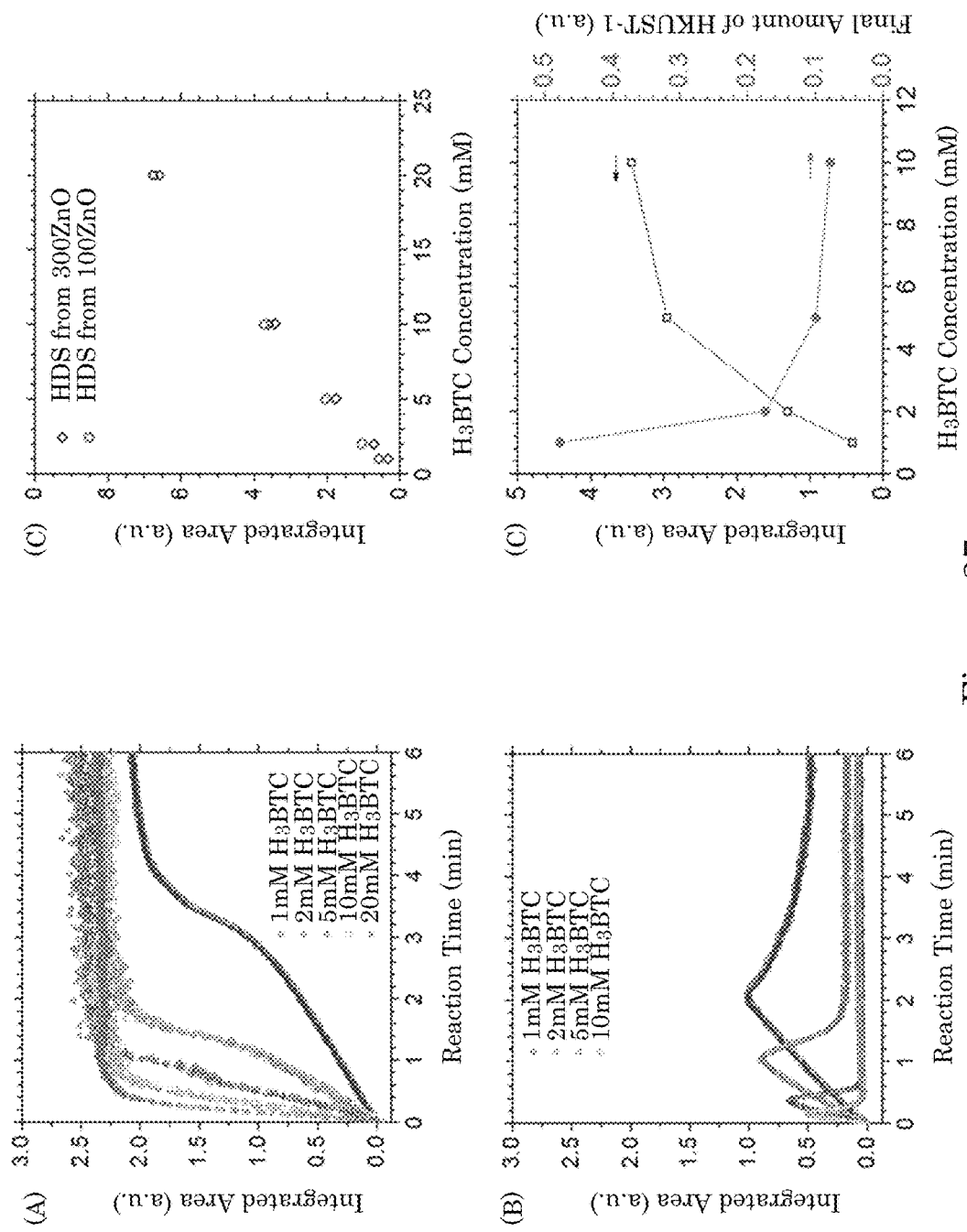
FIG. 27 shows shows graphs of integrated area versus reaction time in panels A and B, initial reaction rate versus concentration in panel C, and delamination rate versus concentration in panel D.

The kinetics for the conversion of (Zn,Cu) HDS to HKUST-1 was monitored via the $v_{as}(OCO^-)$ peak at ~1647 $cm^{-1}$. HDS thin films in a presence as well is an absence of ZnO interfacial layers were synthesized from 300 cycles and 100 cycles of ALD ZnO, respectively. The concentration of $H_3BTC$ solutions used were from 1 mM to 20 mM. Panel A of FIG. 27 shows formation of HKUST-1 from HDS in presence of ZnO interfacial layer. The area of the $v_{as}(OCO^-)$ peak increased and became constant during maximum conversion of HDS. The initial reaction rate obtained from the slope of the curves increase approximately linearly with $H_3BTC$ concentration is shown in Panel C of FIG. 27, indicating a first order reaction kinetics. For 2 mM~20 mM of $H_3BTC$, the total amounts of HKUST-1 formed on the surface were be almost identical.

Panel B of FIG. 27 shows data for formation of HKUST-1 from HDS in an absence of the ZnO interfacial layer. The initial rates increased linearly with $H_3BTC$ concentration is shown in panel C of FIG. 27 and was close to the rates for thick HDS films with ZnO interfacial layers. The peak area of $v_{as}(OCO^-)$ decrease after initial growth because film delamination occurred during the flow. Sparse islands of HKUST-1 films were observed on these substrates. The slope of the decreasing signal provided the rate of net loss ($r_{NL}$) of HKUST-1 on the surface, which included film growth rate and delamination rate. As the concentration of $H_3BTC$ decreased from 10 mM to 1 mM, $r_{NL}$ was reduced by 88%. Consequently, the final amount of HKUST-1 remaining on the surface when 1 mM of $H_3BTC$ was used with greater than 5 times more than that for 10 mM $H_3BTC$.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. An attenuated total reflection flow cell comprising:
   a source prism that communicates source light;
   an internal reflection member mechanically coupled to the source prism and disposed in optical communication with the source prism such that the internal reflection member:
      receives the source light from the source prism;
      optically propagates the source light in a plurality of reflections between a first surface of the internal reflection member and a second surface of the internal reflection member; and
      produces attenuated reflected light in response to attenuated reflectance of the source light at the first surface;
   an exit prism mechanically coupled to the internal reflection member and disposed in optical communication with the internal reflection member such that the exit prism receives the attenuated reflected light from the internal reflection member;
   a flow member mechanically coupled to the internal reflection member and disposed in fluid communication with the first surface of the internal reflection member, the flow member comprising:
      a channel wall disposed in the flow member and opposing the first surface; and
      a flow channel bounded by the channel wall such that flow channel is interposed between the channel wall and the first surface to provide a fluid in the flow channel so that the fluid contacts the first surface,
   such that the source light produces an evanescent wave at the first surface that is received by the fluid at the first surface to produce the attenuated reflected light received by the exit prism.

2. The attenuated total reflection flow cell of claim 1, further comprising:
   a platen on which a portion of the internal reflection member is disposed.

3. The attenuated total reflection flow cell of claim 2, wherein the portion of the internal reflection member that is disposed on the platen comprises the first surface that is in fluid communication with the flow channel.

4. The attenuated total reflection flow cell of claim 2, wherein the platen comprises:
   a contact surface in thermal contact with the internal reflection member; and
   a heater to heat the internal reflection member to a selected temperature.

5. The attenuated total reflection flow cell of claim 2, further comprising:
   a plurality of prism pads,
   wherein the source prism is disposed on a first prism pad, and
   the exit prism is disposed on a second prism pad.

6. The attenuated total reflection flow cell of claim 5, wherein the prism pads independently comprise a metal, a polymer, a glass, a ceramic, or a combination comprising at least one of the foregoing materials.

7. The attenuated total reflection flow cell of claim 5, wherein the platen is disposed on the prism pads.

8. The attenuated total reflection flow cell of claim 7, further comprising:
   a plurality of clamps,
   wherein the first prism pad is disposed on a first clamp, and
   the second prism pad is disposed on a second clamp.

9. The attenuated total reflection flow cell of claim 8, wherein a portion of the platen is disposed on the clamps.

10. The attenuated total reflection flow cell of claim 1, further comprising a seal interposed between the first surface of the internal reflection member and the flow member to constrain a flow of the fluid to the flow channel.

11. The attenuated total reflection flow cell of claim 10, wherein the seal comprises an elastomer.

12. The attenuated total reflection flow cell of claim 1, wherein the source prism and the exit prism independently comprise a material that optically transmits the source light comprising a wavelength from 250 nm to 5000 nm.

13. The attenuated total reflection flow cell of claim 12, wherein the source prism and the exit prism independently comprise germanium, silicon, quartz, or a combination comprising at least one of the foregoing materials.

14. The attenuated total reflection flow cell of claim 1, wherein the internal reflection member comprises a material that optically transmits the source light comprising a wavelength from 250 nm to 5000 nm.

15. The attenuated total reflection flow cell of claim 14, wherein the internal reflection member comprises germanium, silicon, quartz, or a combination comprising at least one of the foregoing materials.

16. The attenuated total reflection flow cell of claim 14, wherein the internal reflection member comprises a silicon wafer comprising a thickness from 100 micrometers to two millimeters.

17. The attenuated total reflection flow cell of claim 9, wherein the internal reflection member is detachably disposed on the platen and substitutable with a second internal reflection member.

18. The attenuated total reflection flow cell of claim 1, wherein a flow direction of the fluid in the flow channel of the flow member is orthogonal to a direction of propagation of the source light in the internal reflection member.

19. The attenuated total reflection flow cell of claim 1, wherein a flow direction of the fluid in the flow channel of the flow member is parallel to a direction of propagation of the source light in the internal reflection member.

20. An attenuated total reflection flow system comprising:
the attenuated total reflection flow cell of claim 1;
a first flow line in fluid communication with the flow channel to provide the fluid to the flow channel;
a second flow line in fluid communication with the flow channel to receive the fluid from the flow channel;
a first mirror to communicate the source light from a light source to the source prism; and
a second mirror to receive the attenuated reflected light from the exit prism to a detector.

* * * * *